(12) United States Patent
Davis et al.

(10) Patent No.: US 11,809,498 B2
(45) Date of Patent: Nov. 7, 2023

(54) OPTIMIZING K-MER DATABASES BY K-MER SUBTRACTION

(71) Applicant: International Business Machines Corporation, Armonk, NY (US)

(72) Inventors: Matthew A. Davis, San Jose, CA (US); Mark Kunitomi, San Francisco, CA (US); James H. Kaufman, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 512 days.

(21) Appl. No.: 16/676,607

(22) Filed: Nov. 7, 2019

(65) Prior Publication Data
US 2021/0141833 A1    May 13, 2021

(51) Int. Cl.
| | |
|---|---|
| *G06G 7/48* | (2006.01) |
| *G06F 16/906* | (2019.01) |
| *G06F 16/901* | (2019.01) |
| *G06F 16/903* | (2019.01) |
| *G06F 16/908* | (2019.01) |
| *G06N 20/00* | (2019.01) |
| *G16B 50/00* | (2019.01) |
| *G16B 10/00* | (2019.01) |

(52) U.S. Cl.
CPC .......... *G06F 16/906* (2019.01); *G06F 16/908* (2019.01); *G06F 16/9027* (2019.01); *G06F 16/90348* (2019.01); *G06N 20/00* (2019.01); *G16B 10/00* (2019.02); *G16B 50/00* (2019.02)

(58) Field of Classification Search
CPC ............... G06F 16/906; G06F 16/9027; G06F 16/90348; G06F 16/908; G06N 20/00; G16B 50/00
USPC ........................................................ 707/722
See application file for complete search history.

(56) References Cited

U.S. PATENT DOCUMENTS

| | | | | |
|---|---|---|---|---|
| 2018/0365375 | A1* | 12/2018 | Flygare ................. | G16B 40/20 |
| 2019/0318807 | A1* | 10/2019 | O'Hara ................ | C12Q 1/6888 |
| 2021/0202040 | A1* | 7/2021 | Williams ............... | G16B 20/40 |
| 2021/0249102 | A1* | 8/2021 | Hurwitz ................ | G16B 40/30 |

FOREIGN PATENT DOCUMENTS

WO    20162172643 A2    10/2016

OTHER PUBLICATIONS

Ondov, Brian D., et al. "Mash: fast genome and metagenome distance estimation using MinHash." Genome biology 17.1 (2016): 1-14.*
Amati, Giambattista, et al. "Estimation of distance-based metrics for very large graphs with MinHash Signatures." 2017 IEEE International Conference on Big Data (Big Data). IEEE, 2017.*
Altschul et al., "Basic Local Alignment Search Tool," J. Mol. Biol. (1990) 215, pp. 403-410.
Camacho et al., "BLAST+: architecture and applications" BMC Bioinformatics, 2009, 10, 421.
Ondov et al., "Mash: fast genome and metagenome distance estimation using MinHash," Genome Biology (2016) 17:132.
Rohlf, "Algorithm 76. Hierarchical clustering using the minimum spanning tree" The Computer Journal, Jan. 1973 16, 93-95.
Sibson, "SLINK: An optimally e cient algorithm for the single-link cluster method" The Computer Journal, Jan. 1973, 16, 30-34.
Wood et al., "Kraken: ultrafast metagenomic sequence classification using exact alignments" Genome Biology, 2014, 15:R46.

* cited by examiner

*Primary Examiner* — Anna Skibinsky
(74) *Attorney, Agent, or Firm* — CANTOR COLBURN LLP; David Mattheis

(57) ABSTRACT

Methods are disclosed for reducing the size of a k-mer reference database used for queries and/or taxonomic classifications when available computer storage and/or memory are inadequate. The k-mers of the reference database have been previously classified to a taxonomy, preferably based on genetic distances. In one method, the k-mers are separated into one or more groups followed by removing k-mers common to the groups. In another method, k-mers are removed based on a selected taxonomic threshold level. A third method combines the features of the previous two methods. The methods are adaptable to machine learning.

19 Claims, 10 Drawing Sheets

| self-consistentID | kmer hits | ref_ID1 | prob(1) | ref_ID2 | prob(2) | ref_ID3 | prob(3) | ref_ID4 | prob(4) | ref_ID5 | prob(5) | ref_ID6 | prob(6) |
|---|---|---|---|---|---|---|---|---|---|---|---|---|---|
| 318856 | 250170 | 1350 | 1.0000 | | | | | | | | | | |
| 325910 | 247573 | 590 | 0.0003 | 1301 | 0.9997 | | | | | | | | |
| 327580 | 247153 | 590 | 0.0003 | 1301 | 0.9997 | | | | | | | | |
| 328523 | 224345 | 1279 | 0.0188 | 1350 | 0.9779 | 561 | 0.0006 | 1578 | 0.0006 | 1485 | 0.0006 | 1637 | 0.0013 |

FIG. 7

FIG. 8A
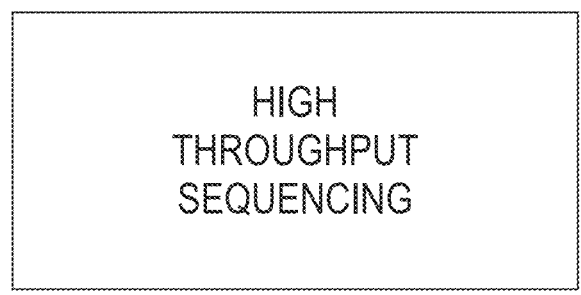
FIG. 8B
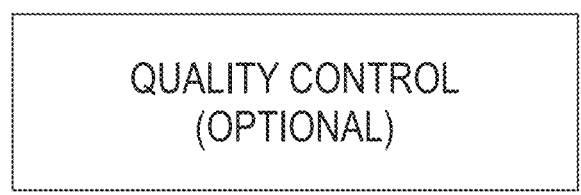
FIG. 8C
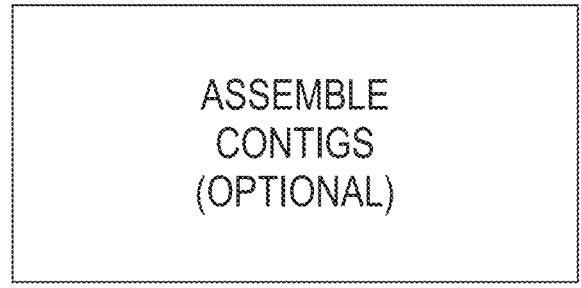
FIG. 8D

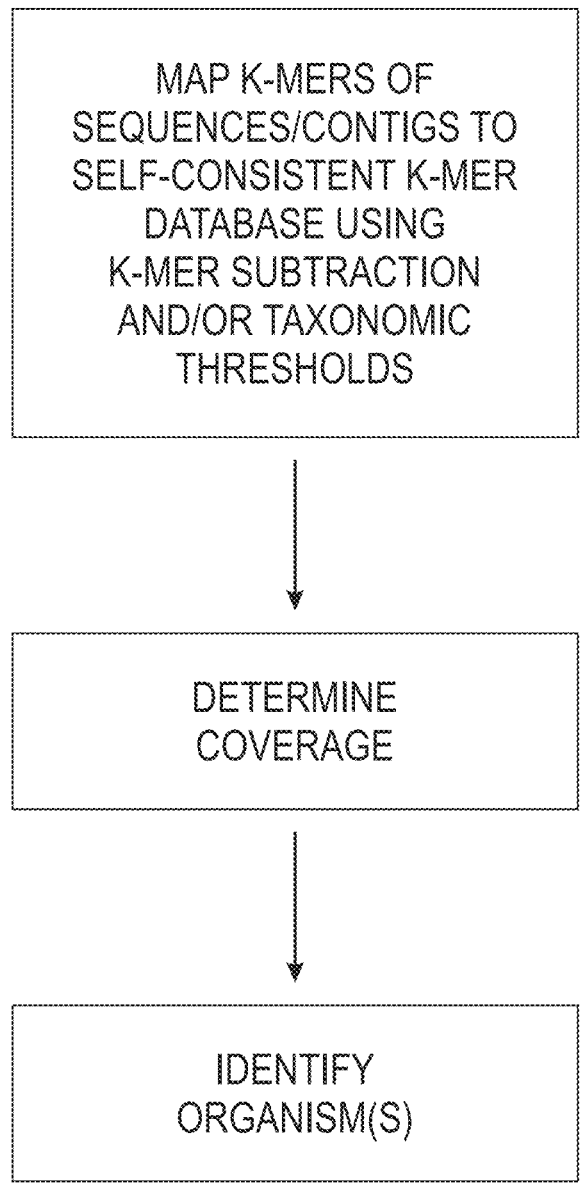

OPTIMIZING K-MER DATABASES BY K-MER SUBTRACTION

BACKGROUND

The present invention relates to optimizing k-mer databases by k-mer subtraction, and more specifically, to reducing the size of k-mer databases when available computer storage and/or memory are inadequate.

Identification of any given unidentified organism from nucleic acid sequence data derived from a sample of that organism (e.g., environmental, medical, food) currently relies on heuristic methods to match the sequence data to a database of known sequences. A nucleic acid sequence that is shared by multiple organisms within the database cannot provide a definitive identity to the unidentified organism. However, the knowledge that this sequence is shared prevents the false identification of any of these multiple organisms. A major problem is that databases cannot be infinitely large, and sequences of greater and lesser discriminatory power occupy the same space per nucleotide. Therefore, inclusion of ambiguous information can limit the inclusion of sequences with greater discriminatory potential. The large amount of currently available public data challenges the standard methods of database construction and use of those databases in most systems, and highlights the need for methods that discriminate what data should be included versus omitted in the databases.

Many methods exist for sequence identification that utilize a database of labeled sequences and software such as Kraken, Mash, and Blast+. Kraken and Mash use a k-mer based approach for comparing nucleic acid sequence data. Kraken uses this approach for assigning taxonomic labels to metagenomic DNA sequences. Mash uses k-mer 'sketches' (subsets of the entire set of k-mers) in order to compare sets of sequences and produce a distance metric. Blast+ stands for basic local alignment search tool. Blast+ uses heuristics rather than exact matching to optimally align search sequences of user-defined length to sequences of a reference database. However, Kraken, Mash and Blast+ have no means to filter what sequences go into their respective database and sketches. This leads to databases that are often too large to store or to load into memory on laptop/desktop computers.

Foreign patent application publication WO2016172643 A2 entitled "Methods and systems for multiple taxonomic classification" assigns weights to k-mers for the identification of constituents of a metagenomic sample. This method is used in order to properly discriminate the source of a given k-mer when it is found in two or more groups of organisms. However, this method does not reduce the database size in any form.

A need exists for methods that minimize size of reference k-mer databases while at the same time improving specificity of taxonomic identifications made with the reference k-mer databases.

SUMMARY

Accordingly, a method is disclosed, comprising:
providing a database comprising k-mers of one or more organisms classified to a taxonomy;
dividing the database into two or more groups of k-mers, wherein each of the groups comprises a unique set of nodes of the taxonomy, wherein all k-mers of a given node reside in only one of the groups; and
removing k-mers common to two or more of the groups, thereby forming two or more modified groups, each of the modified groups containing a unique set of k-mers;
wherein
the modified groups are capable of serving as reference k-mers for computer queries and/or for taxonomic classifications of k-mers of a sample comprising taxonomically unclassified sequenced nucleic acids of one or more organisms.

Another method is disclosed, comprising:
providing a database comprising k-mers of one or more organisms classified to a taxonomy;
assigning a taxonomic threshold level of the taxonomy; and
removing k-mers of the database that are classified to taxonomic levels above the threshold level, thereby forming a modified database having a size in bytes less than the database;
wherein
the modified database is capable of serving as a k-mer reference database for computer queries and/or for taxonomic classifications of k-mers of a sample comprising taxonomically unclassified sequenced nucleic acids of one or more organisms.

Yet another method is disclosed, comprising:
providing a database comprising k-mers of one or more organisms classified to a taxonomy;
assigning a taxonomic threshold level of the taxonomy; and
removing k-mers of the database that are classified to taxonomic levels above the threshold level, thereby forming a modified database;
dividing the modified database into two or more groups of k-mers, wherein each of the two or more groups comprises a unique set of nodes of the taxonomy and all k-mers of a given node reside in one of the groups;
removing k-mers common to the two or more groups, thereby forming two or more modified groups of k-mers;
wherein
the modified groups are capable of serving as reference k-mers for computer queries and/or for taxonomic classifications of k-mers of a sample comprising taxonomically unclassified sequenced nucleic acids of one or more organisms.

Also disclosed is a computer program product, comprising a computer readable hardware storage device having a computer-readable program code stored therein, said program code configured to be executed by a processor of a computer system to implement a method comprising:
providing a database comprising k-mers of one or more organisms classified to a taxonomy;
dividing the database into two or more groups of k-mers, wherein each of the groups comprises a unique set of nodes of the taxonomy, wherein all k-mers of a given node reside in one of the groups; and
removing k-mers common to two or more of the groups, thereby forming two or more modified groups, each of the modified groups containing a unique set of k-mers;
wherein
the modified groups are capable of serving as reference k-mers for computer queries and/or for taxonomic classifications of k-mers of a sample comprising taxonomically unclassified sequenced nucleic acids of one or more organisms.

Another computer program product is disclosed, comprising a computer readable hardware storage device having a computer-readable program code stored therein, said program code configured to be executed by a processor of a computer system to implement a method comprising:

providing a database comprising k-mers of one or more organisms classified to a taxonomy;

assigning a taxonomic threshold level of the taxonomy; and removing k-mers of the database that are classified to taxonomic levels above the threshold level, thereby forming a modified database having a size in bytes less than the database;

wherein the modified database is capable of serving as a k-mer reference database for computer queries and/or for taxonomic classifications of k-mers of a sample comprising taxonomically unclassified sequenced nucleic acids of one or more organisms.

Still another computer program product is disclosed, comprising a computer readable hardware storage device having a computer-readable program code stored therein, said program code configured to be executed by a processor of a computer system to implement a method comprising:

providing a database comprising k-mers of one or more organisms classified to a taxonomy;

assigning a taxonomic threshold level of the taxonomy;

removing k-mers of the database that are classified to taxonomic levels above the threshold level, thereby forming a modified database;

dividing the modified database into two or more groups of k-mers, wherein each of the two or more groups comprises a unique set of nodes of the taxonomy and all k-mers of a given node reside in one of the groups; and removing k-mers common to the two or more groups, thereby forming two or more modified groups of k-mers;

wherein the modified groups are capable of serving as reference k-mers for computer queries and/or for taxonomic classifications of k-mers of a sample comprising taxonomically unclassified sequenced nucleic acids of one or more organisms.

Also disclosed is a system comprising one or more computer processor circuits configured and arranged to:

provide a database comprising k-mers of one or more organisms classified to a taxonomy;

divide the database into two or more groups of k-mers, wherein each of the groups comprises a unique set of nodes of the taxonomy, wherein all k-mers of a given node reside in one of the groups; and remove k-mers common to two or more of the groups, thereby forming two or more modified groups, each of the modified groups containing a unique set of k-mers;

wherein the modified groups are capable of serving as reference k-mers for computer queries and/or for taxonomic classifications of k-mers of a sample comprising taxonomically unclassified sequenced nucleic acids of one or more organisms.

Another system is disclosed, comprising one or more computer processor circuits configured and arranged to:

provide a database comprising k-mers of one or more organisms classified to a taxonomy;

assign a taxonomic threshold level of the taxonomy; and remove k-mers of the database that are classified to taxonomic levels above the threshold level, thereby forming a modified database;

divide the modified database into two or more groups of k-mers, wherein each of the two or more groups comprises a unique set of nodes of the taxonomy and all k-mers of a given node reside in one of the groups;

remove k-mers common to the two or more groups, thereby forming two or more modified groups of k-mers;

wherein the modified groups are capable of serving as reference k-mers for computer queries and/or for taxonomic classifications of k-mers of a sample comprising taxonomically unclassified sequenced nucleic acids of one or more organisms.

Still another system is disclosed, comprising one or more computer processor circuits configured and arranged to:

provide a database comprising k-mers of one or more organisms classified to a taxonomy;

assign a taxonomic threshold level of the taxonomy; and remove k-mers of the database that are classified to taxonomic levels above the threshold level, thereby forming a modified database;

divide the modified database into two or more groups of k-mers, wherein each of the two or more groups comprises a unique set of nodes of the taxonomy and all k-mers of a given node reside in one of the groups; and remove k-mers common to the two or more groups, thereby forming two or more modified groups of k-mers;

wherein the modified groups are capable of serving as reference k-mers for computer queries and/or for taxonomic classifications of k-mers of a sample comprising taxonomically unclassified sequenced nucleic acids of one or more organisms.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIG. 7 is a sample of tabulated probabilistic report data available after k-mer analysis of sample data using the self-consistent k-mer database.

FIGS. 8A-8G depict a flow diagram for a process of profiling nucleic acids of a sample using the self-consistent k-mer database.

DETAILED DESCRIPTION

Methods are disclosed that improve computational performance of taxonomic queries by minimizing storage space used by k-mer databases, reducing computer memory requirements, and increasing speed of queries. The methods can further improve specificity of returned results of k-mer based taxonomic queries.

Herein, genome databases that contain inconsistently classified sequence data are referred to as "standard databases." The taxonomy of standard databases is referred to herein as a "standard taxonomy." Standard databases include the downloadable genome databases of the National Center for Biotechnology Information (NCBI). Genome databases whose k-mers are classified to a self-consistent taxonomy are referred to herein as self-consistent k-mer databases. A self-consistent taxonomy does not depend on the metadata associated with the k-mers. Preferably, the self-consistent taxonomy is based on a calculated genetic distance after features associated with mobile elements have been removed. Mobile elements include plasmids and conjugative transposons that can move between taxa. K-mers associated with mobile elements should be removed from genomes even if the mobile elements are found in only one genome. Methods of forming self-consistent k-mer databases are disclosed in U.S. patent application Ser. Nos. 16/147,779 and 16/226,995, discussed in more detail further below. For the presently disclosed methods utilizing k-mer subtraction, it is preferable that the k-mers be classified beforehand to a self-consistent taxonomy. This simplifies removal of k-mers. For example, with Kraken, if the database is built with k-mers, then k-mers common across taxa tend have a lowest common ancestor (LCA) towards the top of the tree. These common k-mers can be removed simply by picking a rank above which k-mers are deemed "too common". An exception to the 'preferable' sentence is there may be instances when the number of k-mers is so large that the database will not fit in memory until/unless some are removed. In that case, k-mers to be removed can be identified simply by comparing a few genomes from very different taxa, finding the common kmers, and removing those before classifying the remaining k-mers to a self-consistent taxonomy.

A preferred method of reducing the size of a k-mer database comprises sub-dividing the database into two or more groups and removing k-mers common to the two or more groups. Each group can contain k-mers associated with one or more organisms. Removing k-mers from a k-mer database or from a group of k-mers is referred to as "k-mer subtraction." The removed k-mers can be discarded or stored in a separate k-mer electronic file. K-mer subtraction allows queries and classifications when the reference database size exceeds the available computer storage and/or computer memory.

Figure 1:
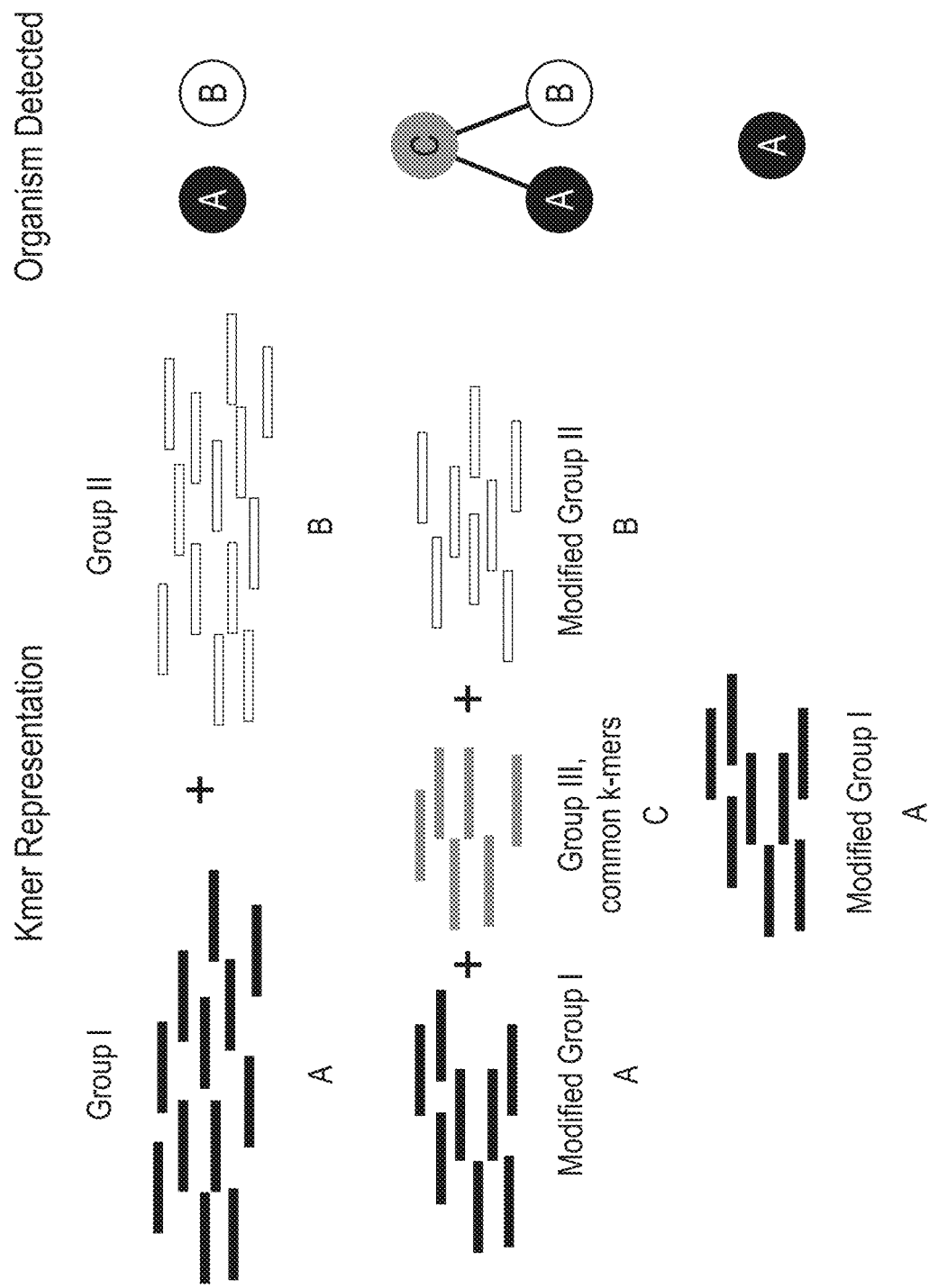
FIG. 1 is a diagram illustrating an example of k-mer subtraction.

A non-limiting example k-mer subtraction is illustrated in the diagram of FIG. 1. In this example, a k-mer database contains classified k-mers for organism A and organism B. The database is too large for available computer storage and/or computer memory. To overcome this challenge, the database is sub-divided into two or more groups. Each of the groups comprises a unique set of nodes of the taxonomy, and all k-mers of a given node reside in a single group. For example, a first group of classified k-mers designated "group I" includes a node for organism A. The remaining set of classified k-mers designated "group II" includes a node for organism B. Groups I and II are independent sets of data files. Groups I and II can share common k-mers that were classified to different nodes of the taxonomy. The common k-mers can cause an unknown organism of a sample to be classified as organism A and organism B. Herein, a "sample" means any sample containing sequenced DNA and/or RNA of one or more organisms (e.g., environmental samples, medical samples, food samples, comprising one or more microbes) that is taxonomically unclassified. The common k-mers shared by the two or more groups (e.g., groups I and II) are then removed (subtracted) from the groups, producing, respectively, two or more modified groups (e.g., modified groups I and II), each of smaller size in bytes. Another group (e.g., group III) contains the removed common k-mers, which can be stored or discarded. In this example, modified group I comprises k-mers unique to group I, which includes organism A. Modified group II comprises k-mers unique to group II, which includes organism B. FIG. 1 shows that by removing the common k-mers, an unknown organism of a sample can potentially be more accurately classified (e.g., in this case as organism A) using modified group I and modified group II as the reference k-mers.

If available computer storage and/or computer memory is inadequate for modified group I and modified group II together, then the database can be subdivided further into smaller groups before removing the common k-mers. After k-mer subtraction, each of the smaller groups contains a unique set of k-mers.

More specifically, the method comprises i) providing a database comprising k-mers of one or more organisms classified to a taxonomy, ii) dividing the database into two or more groups, wherein each of the two or more groups comprises a unique set of nodes of the taxonomy and all k-mers of a given node reside in a single one of the groups (e.g., one could pick groups from a very high taxonomic rank (e.g., phylum) such as Firmicutes and Proteobacteria, which represent two such distantly related groups (phyla) of bacteria (e.g., *Listeria* and *Salmonella*, respectively) having distantly related genomes), and iii) removing k-mers common to the two or more groups, thereby forming two or more modified groups, each of the two or more modified groups containing a unique set of k-mers. The modified groups are capable of serving as reference k-mers for classifying a set of unclassified k-mers of a sample to the taxonomy, where the sample comprises sequenced nucleic acids of one or more organisms. Preferably, the k-mers of the database are classified to a self-consistent taxonomy that is independent of metadata associated with the k-mers. A preferred self-consistent taxonomy is one based on genetic distance. The two or more modified groups can be stored on different computer nodes or the same computer node when performing a classification or query.

The process of classifying k-mers of a sample can be performed using the two or more modified groups in parallel (i.e., operating on the two or more modified groups simultaneously) or in sequence (e.g., operating on one of the groups at a time).

A second method reduces the size of a k-mer database by removing k-mers based on a given threshold of taxonomic specificity (i.e., based on a rank or level of the taxonomic tree). Taxonomic levels for microbes include domain, kingdom, division, phylum, class, order, family, genus, species, sub-species, and strain. When k-mers of an organism are classified to a taxonomy they are compared with other k-mers for uniqueness. K-mers that are not unique are classified by determining their respective lowest common ancestors (LCAs) of the taxonomic tree and assigning these k-mers to their respective LCAs. K-mers of the database can be assessed for specificity based on their assigned levels of the taxonomic tree. K-mers can be retained or removed from the database based on a threshold taxonomic level (rank) assigned by the user. Removing k-mers above the assigned threshold level results in a minimized set of k-mers (i.e., modified database) requiring less computer memory. The minimized set can serve as a reference k-mer database when performing classifications or queries of sequenced samples.

More specifically, the method comprises i) providing a database comprising k-mers classified to a taxonomy, ii) assigning a taxonomic threshold level of the taxonomy, and iii) removing k-mers of the database that are classified to taxonomic levels above the threshold level, thereby forming a modified database having a size in bytes less than the database. The modified database is capable of serving as a k-mer reference database for computer queries and/or for taxonomic classifications of k-mers of a sample comprising unclassified sequenced nucleic acids of one or more organisms. In an embodiment, the k-mers of the database are classified to a self-consistent taxonomy based on genetic distance. In another embodiment, the taxonomic threshold level is selected from the group consisting of family, genus, species, sub-species, and strain.

A third method is disclosed that combines features of the previous two methods. In this method, the k-mer database is modified by removing k-mers classified to higher taxonomic levels than a threshold level assigned by the user. The resulting modified database is then divided into two or more groups of k-mers. K-mers common to the two or more groups are removed, thereby forming two or more modified groups of k-mers, each of the modified groups containing a unique set of k-mers. The modified groups can serve as reference k-mers when performing a query and/or classification of a sample containing unclassified sequenced nucleic acids of one or more organisms.

More specifically, the method comprises i) providing a database comprising k-mers classified to a taxonomy, ii) assigning a taxonomic threshold level of the taxonomy, iii) removing k-mers of the database classified to taxonomic levels above the threshold level, thereby forming a modified database, iv) dividing the modified database into two or more groups of k-mers, wherein each of the two or more groups comprises a unique set of nodes of the taxonomy and all k-mers of a given node reside in one of the groups, and v) removing k-mers common to the two or more groups, thereby forming two or more modified groups of k-mers. The modified groups are capable of serving as reference k-mers for computer queries and/or for taxonomic classifications. In an embodiment, the k-mers of the database are classified to a self-consistent taxonomy based on genetic distance.

Utility

K-mer substraction based on a user-defined threshold level reduces database file size, thereby decreasing query times and reducing computer storage and memory requirements. K-mer subtraction based on dividing a database into groups also decreases query times, reduces computer storage and memory requirements, allows partitioning of the groups across two or more computer nodes, and permits parallel processing of the groups. Moreover, the common k-mers can be partitioned onto a separate computer node and used for identification confirmation purposes. K-mer subtraction can reduce false positive identifications when querying a database, increase specificity of organism identification, and/or allow users to omit organisms, genes, protein, and/or protein domains when searching genome data, gene data, protein data, and protein domains, respectively. The above-disclosed methods are adaptable to machine learning. In an embodiment, the taxonomic threshold level is selected by a machine using artificial intelligence (i.e., without human intervention).

Self-Consistent Taxonomy

Classic (standard) taxonomy for bacteria in biology was defined by phenotype (observations under a microscope) absent any information about genotype (genetic data). Now that large amounts of genome data are available, it is apparent that hierarchical clustering based on whole genome distance does not map in a simple 1:1 relationship to the standard taxonomy. Standard taxonomic classification of microbes in official databases (e.g., the National Center for Biotechnology Information (NCBI) Sequence Read Archive (SRA) and NCBI Genbank) contain many errors. Metadata of the standard databases are in error for hundreds of organisms, with genomes receiving the wrong identification (ID). The taxonomic tree is also inaccurate and routinely changes as new genomes are added to NCBI or other public databases. This causes two problems: i) a k-mer database built with the inaccurate and error-filled standard taxonomy loses the ability to accurately identify specific taxa (e.g., genera are not named correctly) and ii) when this sub-optimal database is used to identify newly sequenced organisms, a large fraction of the sequence data from the new organisms may go unidentified or become inaccurately named, resulting in the final identification being simply wrong. An incorrect classification can lead to the wrong name at each level of the taxonomic tree. There are too many errors and too many unusual genotypes to manually curate the hundreds of thousands of genomes available.

For the above reasons, inconsistently classified sequence data are preferably re-classified to a self-consistent taxonomy before use in the disclosed methods.

The self-consistent k-mer database preferably comprises a map that links self-consistent identifications (IDs) of the self-consistent taxonomy to the standard IDs of the standard taxonomy, thereby preserving the standard taxonomic labeling while remaining insensitive to the errors of the standard taxonomy.

Definitions

The following definitions are applicable.

Abbreviations A, C, G, and T refer to nucleotide bases adenine, cytosine, guanine, and thymine, respectively.

A "clade" is a group of biological taxa (such as species) that includes all descendants of one common ancestor.

A "contig" is a set of overlapping DNA sequences that together represent a consensus sequence of DNA or a region thereof.

A "consensus sequence" is the calculated order of the most frequent residues found at each position in a sequence alignment.

"Copy number" means the number of copies of a gene or plasmid within a genome. The copy number can vary from individual to individual.

"Coverage" or "depth of coverage" is the number of times a given sequence from a genome is represented in the set of sequences derived from that genome.

"DNA" is deoxyribonucleic acid.

A "protein domain" is a region of a protein having a particular shape and/or function.

A "false positive" is output that incorrectly indicates that a particular condition or attribute is present.

A "gene" is the basic unit of heredity, a linear sequence of nucleotides along a segment of DNA that provides the coded instructions for synthesis of RNA, which, when translated into protein, leads to the expression of a hereditary trait.

"Genetic distance" is a quantitative measure of the divergence of one or more regions of DNA and/or RNA between species or populations of species. Genetic distance can be based on whole genome-whole genome distances, gene-gene distances, protein domain-protein domain distances (i.e., the portions of the DNA encoding for a particular protein domain), protein-protein distances (i.e., the portions of the DNA encoding for a whole protein), or protein domain-protein domain distances based on an amino acid distance metric. More specifically, genetic distance is a measure of the differences in nucleotide sequences of the k-mers with respect to whole genomes, genes, and/or other genetic regions of interest. Thus, the average number of codon or nucleotide differences per gene can be a measure of genetic distance. Genetic distance is a numeric distance calculated between each pair of genomes of the standard database using, for example, MASH (which utilizes the MinHash algorithm). The MinHash algorithm calculates distance from a Jaccard index. The Jaccard index is calculated from "sketches" of the k-mers, which are diagrams showing the similarity and differences between k-mers of the pair of genomes.

A "genome" is the total genetic content of a microorganism. In the case of bacteria, the genome is DNA.

A "ground truth dataset" is a dataset formed by direct observation (measured data) as opposed to data obtained by inference or assumption.

Herein "high-throughput sequencing" (HTS) is any method of sequencing a nucleic acid that is highly parallel and does not involve cloning the nucleic acid. A genome or metagenome is cut into a large number of fragments, and the fragments are sequenced in parallel.

"Homology" refers to the similarity of sequences (e.g., DNA, RNA, Protein, etc.) arising from a common ancestry.

"Hybridization" is the formation of double-stranded helix from single-stranded complimentary pairs of DNA and/or RNA by annealing.

The term "k-mer" means a sub-sequence of a read obtained through DNA sequencing having k number of nucleotide base units, where k is a positive whole number greater than 1.

Herein, a "database" comprises one or more electronic files (data tables) for storing and retrieving data. Data tables comprise rows and columns (i.e., fields) of data. The rows are formally called tuples or records. A data table comprises one or more records, each record comprising one or more defined fields having respective defined data types (e.g., text, numeric, date, time, memo, and so on) and defined field lengths where applicable. A working data table comprises at least one record containing data in one or more fields of the record. The data tables are located on data storage devices, which can be remote or local relative to the user input/output devices. A "database system" comprises at least one data table and a database management software program for managing the storage and retrieval of data to and from the data tables. The database management programs can be remote or local relative to the data tables and/or the end user. A Relational Database Management System (RDBMS) is a database management system (DBMS) that uses relational techniques for storing and retrieving data using data tables. A relational database system can have many data tables, and each data table can have multiple records and multiple fields within each record. A data table in a relational database system can be accessed using an index. An index is an ordered set of references (e.g., pointers) to the records or rows in a data table. The index is used to access each record in the file using a key (e.g., one or more of the fields of the record or attributes of the row). Without an index, finding information in a large data table would require a resource-intensive time-consuming scan (e.g., linearly) of each record of a table. Indexes provide a faster alternate technique of accessing data contained in one or more data tables that are linked by a common key. Users can create indexes on a table after the table is built. An index is based on one or more columns (fields) of a given table.

A "k-mer database" is a database in which a given record comprises a field for storing a k-mer of a nucleic acid sequence of one or more organisms. Another field of the record stores a taxonomic ID that associates the k-mer to a lowest common ancestor node (LCA) of a taxonomic tree. As will be described below in more detail, other fields of the record can store standard IDs to a standard taxonomy. Still other fields of the record can store metadata associated with the k-mer and/or the nucleic acid sequence from which the k-mer originated.

Kraken is a taxonomic classifier that assigns taxonomic labels to DNA sequences, including k-mers. Kraken uses k-mers from a sequence read of a sample to query a reference database containing k-mers from reference genomes (i.e., the genomes of RefSeq Complete at NCBI) for matches. The k-mers are self-consistently mapped to the lowest common ancestor (LCA) of all genomes known to contain a given k-mer. Typically, the k value for a k-mer query is 31 but this value can be modified by the user. For typical queries, k can be a positive whole number in the range of about 10 to about 1000.

Herein, a "Kraken database" is an electronic file containing k-mers self-consistently assigned to a taxonomic hierarchy by the Kraken classifier.

A "locus" (plural loci) is a position on a genome (e.g., gene, regulatory element, origin of replication).

A "metagenome" is all the genetic information of a sample.

"Metagenomics" is the analysis or study of metagenomes.

"Metatranscriptome" is the collection of all RNA transcripts of a sample.

"Metatranscriptomics" is the analysis or study of metatranscriptomes.

A "microbiome" is a community of microorganisms that inhabit a particular environment (e.g., microbes of the human gut), or a sample taken therefrom.

"Origin of replication" is the locus at which DNA replication begins.

Operational taxonomic units (OTUs) are used by taxonomy classifier systems (e.g., Kraken classifier) to categorize the k-mers based on sequence similarity. For example, in 16S rRNA metagenomics, OTUs are clusters of similar sequence variants of the bacterial 16S rRNA marker gene sequence. Each cluster represents a taxonomic unit of a bacterial species or genus depending on the sequence similarity threshold. Typically, OTU clusters are defined by a 97% identity threshold of the 16S gene sequences to distinguish bacteria at the genus level. Species separation requires a higher threshold of 98% or 99% sequence identity, or the use of exact sequence variants instead of OTU cluster.

A "plasmid" is a self-replicating extrachromosomal circular DNA that replicates independently of the bacterial chromosome and carries genes for functions not essential for growth.

"RNA" is ribonucleic acid.

"mRNA" refers to messenger RNA. The mRNA codes for amino acid sequences composing proteins.

"rRNA" refers to ribosomal RNA.

"tRNA" refers to transfer RNA. A tRNA transports a specific amino acid to a ribosome for synthesis of a protein.

An "RNA transcript" is an RNA produced through the process of transcription of DNA.

"Sample" means any sample containing DNA and/or RNA capable of undergoing analysis using the disclosed methods.

"Sequencing" refers to a process of determining the precise order of base residues (i.e., nucleotides) in a nucleic acid (e.g., DNA, RNA).

A "sequence" is a fragment of a nucleic acid (e.g., RNA, DNA) that has been sequenced (i.e., the order of the nucleotides bases is known).

A "sequence read" or "read" is a finite length or fragment of a nucleic acid that is output by a sequencing instrument. For example, a read from an Illumina sequencer is 100-150 base pairs in length today. Sequencing may also be done on "paired end" reads where two reads are connected by a spacer (that is not read), increasing the effective read length to 300 or more and covering a larger region of the genome.

A "sequence alignment" is a way of arranging sequences to identify regions of similarity, which may be a consequence of functional, structural, or evolutionary relationships between the sequences.

"Shotgun sequencing" is a quasi-random process in which a nucleic acid is broken up into many random smaller fragments that are individually sequenced. The sequences are ordered based on overlapping regions of genetic code and reassembled into the complete sequence of the nucleic acid.

"Taxonomy" is a biological scheme of classification of organisms. Herein, for bacteria, the hierarchy is domain, kingdom, division, phylum, class, order, family, genus, species, sub-species, and strain. Each of the foregoing classifications is a "rank" or "level" on the taxonomic tree.

A "taxonomic tree" herein is a data structure for classifying organisms. The taxonomic tree comprises nodes (i.e., taxa, singular taxon) that are grouped into "parent nodes" linked to "child nodes". Parent nodes are depicted above child nodes in the tree diagram. Child nodes are taxonomic descendants of parent nodes. For example, a genus (parent node) can be linked to two or more species (child nodes). The taxonomic tree can be rooted (i.e., known ancestral root) or unrooted (i.e., unknown ancestral root), bifurcating (i.e., two child nodes per parent node) or multi-furcating (i.e., more than two child nodes per parent node). Typically, the taxonomic tree is in the form of a "binary tree" (i.e., each parent node has two child nodes). A "leaf node" is a child node having no descendants (e.g., the species of a genus). In the self-consistent taxonomy, each leaf node has one genome. "Internal nodes" are all nodes other than the leaf nodes.

"Transcription" is the process of forming an RNA from a DNA template.

The abbreviation "bp" means "base-pair" (e.g., a read of 100-bp means that one DNA read has 100 nucleotides in the polymer chain.

"Miscalling" refers to a sequencing error where a nucleotide in a sequence read is different from the true nucleotide.

A quality value is an assigned value given to each nucleotide in a sequence read that reflects the likelihood of miscalling the nucleotide. The higher the quality value is, the lower the likelihood of miscalling.

A "reference genome" is a genome from the same species or close species that has already been sequenced.

"Mapping" a sequence read is a process of finding the position or coordinate of a sequence read on the reference genome.

A "perfect match prefix" is a k-mer of a sequence read that is identical to, or a perfect match to, some equal-length k-mer(s) of the reference genome. The k-mer of the sequence read is used to initially anchor the sequence read on the reference genome.

Base substitution: After a sequence read is mapped to the reference genome, certain bases are different from the corresponding bases on the reference genome.

Insertion: Compared with the reference genome, some continuous bases are inserted between two adjacent bases on the sequence read.

Deletion: Compared with the reference genome, the sequence read loses some continuous bases.

INDEL: an insertion or deletion in a read when trying to find the best alignment of a read to a reference genome.

Figure 2:
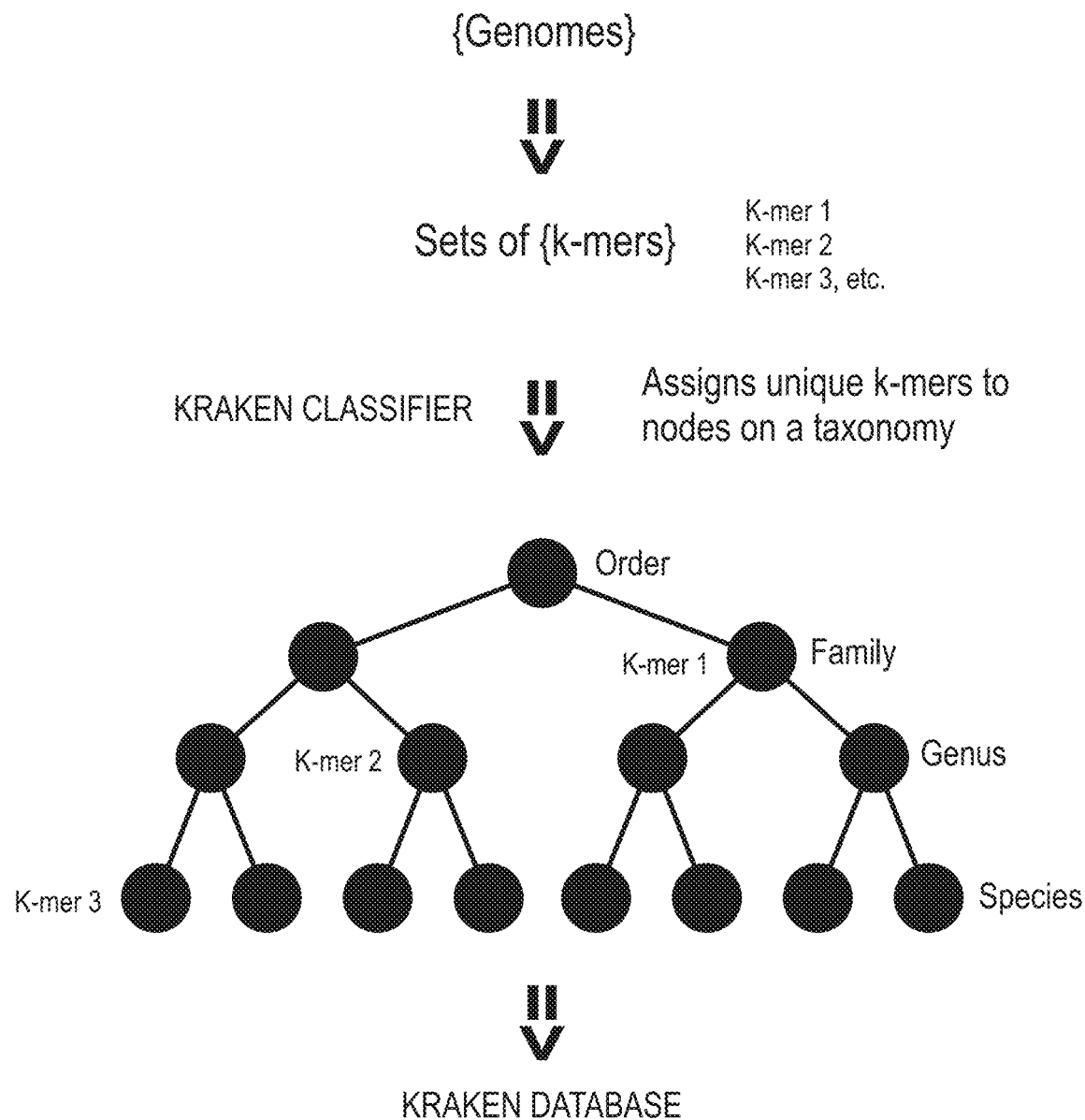
FIG. 2 is a diagram showing an existing process of classifying sequence reads using a Kraken classifier.

FIG. 2 is a diagram showing an existing process of classifying sequence reads using a Kraken classifier. A sample metagenome is sequenced, producing reads of varying base length. In a k-mer based classification method, a standard database is provided using a set of genomes and taxonomy provided by the user. The classifier program (e.g., Kraken classifier, CLARK classifier) scans each k-mer of a given read and consults a standard database (e.g., NCBI RefSeq Complete genomes) which can contain many genomes, for an exact match. During the database build step, all distinct k-mers in a genome set are collected into a (k-mer, taxonomic ID) pair, with the taxonomic ID being assigned from the genome's operational taxonomic unit (OTU) of the standard taxonomy. As distinct k-mers are often shared across multiple organisms (for example, in conserved regions), the individual classification method must provide a mechanism for resolving conflicts. "Conserved sequences" are similar or identical DNA or RNA sequences, which have been maintained by natural selection and are shared by species or within a genome. One method of resolving a conflict is to set a k-mer's taxonomic ID to the lowest common ancestor (LCA) of the two conflicting nodes of the standard taxonomy and reduce the level of taxonomy to the next higher node on the tree. This approach reduces the specificity of a given k-mer while retaining overall sensitivity. Herein, the specificity of a k-mer decreases by moving the k-mer to a higher rank on the taxonomic tree. Sensitivity decreases by increasing the number of nodes at the same rank.

As there are often multiple exact k-mer matches for a given read, the classifier must also resolve conflicts against the taxonomy. When a consensus decision is reached by the software program, taking into account configurable threshold options (e.g., the number of k-mers that must match), the k-mer is declared as either classified and given a taxonomic ID or remains unclassified. A consensus is defined by the majority (largest fraction) of k-mers matching a single or unique lineage. The classified k-mers are assigned to nodes on a taxonomic tree.

The "standard taxonomy" is defined herein as a not-self-consistent taxonomy. A not-self-consistent taxonomy is one in which classifications can be made based on conflicting, incomplete, and/or erroneous input that cause k-mers to be taxonomically misclassified. Conflicting inputs can include errors in metadata. Metadata are any supplemental information added to the records of a database (e.g., information about the taxonomic hierarchy, the k-mers, and/or the reads, and so on). The metadata can be introduced by either the programs operating on the reads, human operators of the programs, or both. The metadata can be used to compare a classification done by the classifier program (e.g., Kraken) with a classification assigned by some other method (e.g., the lab contributing the other metadata) for validation purposes and/or identifying inconsistencies and errors.

Figure 3:
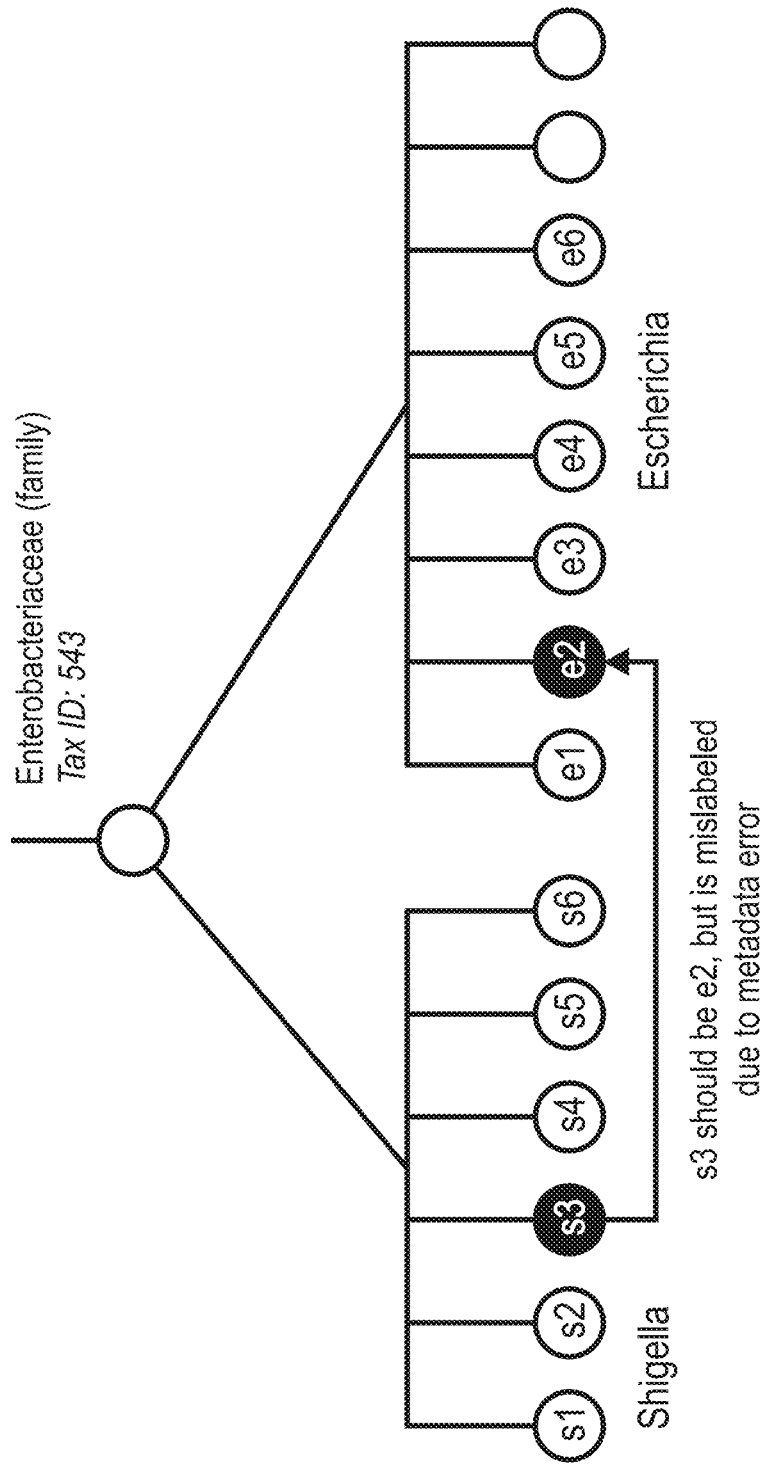
FIG. 3 is a diagram illustrating a partial taxonomic tree containing metadata errors.

FIG. 3 is a diagram illustrating a portion of a standard taxonomy of a standard database containing metadata errors (e.g., the NCBI taxonomy of the genomes of RefSeq Complete). Metadata errors combined with a not-self-consistent taxonomy degrade the ability of a database system to assign a specific organism identification. Genomes at the leaf nodes of the standard taxonomy can be placed there based on manually added taxonomic IDs, which may be incorrect. In this example, the genome indicated as 's3' is incorrectly labeled as a *Shigella* genome and, based on that invalid metadata, placed with other *Shigella* genomes in the tree (indicated by the first character 's'). In fact, this hypothetical genome 's3' is an *Escherichia* genome. It "should be" labeled as *Escherichia* (e.g., 'e2') and placed on the tree with other *Escherichia* species, but it is not. Accordingly, node 'e2' is missing. The mislabeled *Escherichia* genome shares a large number of k-mers with all other *Escherichia* genomes, and when the database is built, k-mers that are shared by nodes at the same level or below on the tree are moved up to the lowest common ancestor (LCA) node (e.g., k-mers common to two or more species nodes move up to a common genus node). The node from which the k-mers move up retains only k-mers unique to that node. In this example, many of the k-mers that should be used to identify the genus *Escherichia* (and distinguish it from the genus *Shigella*) will move up to the Enterobacteriaceae family node in the tree, the LCA of the *Shigella* and *Escherichia* genera, causing a decrease in specificity of the k-mers moved up. This error greatly diminishes the ability of the standard database to identify the two organisms and increases the error in the identification capacity, which can render the information useless, for example, in disease diagnostics.

On the other hand, if the genomes are mapped to a self-consistent taxonomy, the problem with inaccurate or incorrect metadata can be separated from the k-mer classifications and construction of the k-mer database, thereby establishing an accurate classification for each k-mer. A self-consistent taxonomy is defined herein as a taxonomy constructed, preferably exclusively, from calculated genetic distances. Populations with many similar alleles have small genetic distances. This indicates that they are closely related and have a recent common ancestor.

A flow diagram for a method of constructing a k-mer database having a self-consistent taxonomy from a collection of genomes is shown in the flow diagram of FIGS. 4A-4G.

Figure 4:
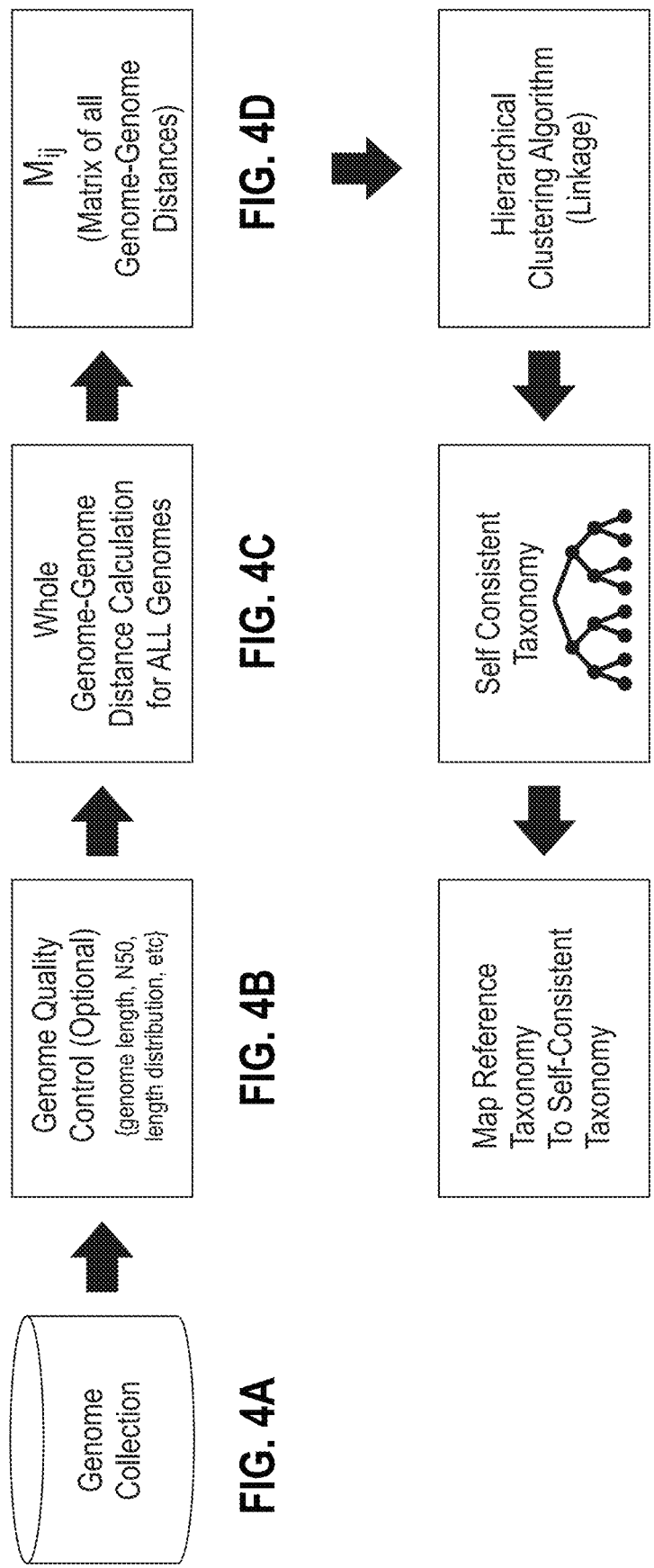
FIGS. 4A-4G depict a flow diagram for a method of constructing a self-consistent taxonomy from any collection of genomes.

The method begins by initially providing a collection of sequenced whole genomes (FIG. 4A). For example, the raw sequences of 360,000 prokaryote genomes can be downloaded from the SRA at the NCBI website, and these can be assembled into genomes. The collection of assembled genomes provides a "sample database" comprising "sample genomes." Almost half of the sample genomes can have either metadata errors, misclassified reads, and/or be of poor quality due to other reasons. The sample genomes can be treated as unclassified k-mers of nucleic acid for the following steps. It should be understood that the metadata in one or more of the sample genomes contains errors in classification in the standard taxonomy. The metadata of the sample genomes can be carried forward into the genomes of the self-consistent k-mer database without affecting the node assignments of the sample genomes in the self-consistent taxonomy.

Optionally, quality control can be performed on the reads of the sample (FIG. 4B). Quality control can include, for example, the removal (trimming) of low-quality reads or segments of reads. Non-limiting trimming algorithms and software programs for cleanup of raw DNA sequence reads include SolexaQA DynamicTrim, FASTX-ToolKit, ConDeTri, NGS QC Toolkit, FASTQC, and Trimmamatic. The result is a "clean sample" generally containing fewer assembled genomes.

Next, the genetic distances are calculated for every pair of genomes of the clean sample (FIG. 4C). The result is a two-dimensional matrix M comprising genetic distances $m_{i,j}$ (FIG. 4D), where each element $m_{ij}$ is a calculated distance between genome i and genome j of the clean sample. Subscripts i and j are index values to each genome of the pair used to calculate distance $m_{ij}$. The distance between every genome and every other genome of the cleaned sample is calculated, resulting in matrix M. Non-limiting methods of calculating genetic distances include the MinHash method, the Meier-Kolthoff method, Cavalli-Sforza chord distance method, the Reynolds, Weir, and Cockerham method, Nei's standard genetic distance method, and pairwise distance method. Pairwise distance methods calculate distances based on differences between all pairs of k-mers in two datasets. Preferably, the genetic distances are calculated using the program MASH (github.com/marbl/Mash) using the MinHash algorithm (ONDOV, et al., "Mash: fast genome and metagenome distance estimation using MinHash," Genome Biology (2016), 17:132). MinHash calculates the distances between all pairs of genomes in the cleaned sample from k-mer "sketches." A sketch is a compressed representation of sequences that allows for tracking k-mer counts and k-mer frequency distributions of a sequence data set without storing the sequence structures themselves, thereby saving computer storage space and memory usage. The sketches are evaluated to produce a Jaccard index, which is used to calculate genetic distances between, in the present instance, pairs of genomes. The calculated distance matrix M for the clean genomes can be gigabytes in size. The disclosed method is not limited to the use of MinHash for calculating the Jaccard index.

Classifying k-Mers to a Self-Consistent Taxonomy

The matrix M serves as input to a hierarchical agglomerative (bottom-up) or divisive (top-down) clustering algorithm (FIG. 4E) to compute a self-consistent taxonomy. For example, the clustering algorithm can be agglomerative single linkage (SLINK) using minimum spanning tree (MST) described respectively by Sibson, R., "SLINK: an optimally efficient algorithm for the single link cluster method," The Computer Journal, 1973, 16:30-34, and Rohlf, F. James, "Algorithm 76. Hierarchical clustering using the minimum spanning tree," The Computer Journal, 1973, 16:93-95. The clustering algorithm computes a new self-consistent taxonomy, which is independent of the standard taxonomy (i.e., the NCBI taxonomy) because it is based exclusively on the calculated genetic distance between the genomes of the clean sample (FIG. 4F). In this example, the self-consistent taxonomy is a binary tree. Each node of the self-consistent taxonomy is assigned a unique self-consistent ID. Each k-mer of the clean sample is assigned to one and only one node of the self-consistent taxonomy.

Other non-limiting agglomerative clustering algorithms include i) complete linkage (CLINK), ii) unweighted pair-group method using arithmetic averages (UPGMA, also called unweighted arithmetic average clustering), iii) weighted arithmetic average clustering (WPGMA, also referred to as "Mcquitty"), iv) Ward method, v) unweighted centroid clustering (UPGMC), and vi) weighted centroid clustering (WPGMC).

A non-limiting example of a divisive clustering algorithm is DIANA (Divisive Analysis Clustering).

In an embodiment, the self-consistent taxonomy is based on genome-genome distances calculated by MinHash. In another embodiment, the self-consistent taxonomy is based on genome-genome distances calculated by the Meier-Koltoff method. In another embodiment, the self-consistent taxonomy is based on genome-genome distances calculated by the Levenshtein distance method (also referred to as "edit distance" based on the number of edits required to convert one string (read) into another). In another embodiment, the self-consistent taxonomy is based on gene-gene distances in which sequence alignments to a known reference genome are performed by a software program MUSCLE (MUltiple Sequence Comparison by Log-Expectation), and genetic distance is calculated using Nei's standard genetic distance method or pairwise distance method.

MUSCLE is a multiple sequence alignment (MSA) software tool. MSA is generally the alignment of three or more biological sequences (protein or nucleic acid) of similar length. Other MSA software tools include Clustal Omega, Kalign, MAFFT, MView, MAFFT_addseq, T-Coffee, and WebPRANK.

Pairwise sequence alignment (PSA) is used to identify regions of similarity between two sequences. Pairwise sequence alignment tools include Needle and Stretcher for global (end-to end) alignment; Water, Matcher, and LALIGN for local alignment; and Genewise for genomic alignment. Other pairwise sequence alignment tools include and Promoterwise and Wise2dba.

Constructing a Self-Consistent k-Mer Database and Circumventing Metadata Errors

The self-consistent taxonomy is then used to construct a k-mer reference database containing the k-mers of the clean sample associated with respective self-consistent IDs.

Mapping the Reference Taxonomy to the Self-Consistent Taxonomy

Next, a map is created associating the self-consistent IDs of the self-consistent taxonomy to the standard IDs of the standard taxonomy (FIG. 4G). In effect, this amounts to re-classifying the smaller number of genomes (k-mers) of the standard database (e.g., RefSeq Complete at NCBI) against the new self-consistent taxonomy while carrying forward the standard IDs and metadata of the standard taxonomy (i.e., standard NCBI taxonomy) into the self-consistent k-mer database. This process was accomplished using a custom software program, where every k-mer of the smaller standard database was assigned a node in the self-consistent taxonomy, thereby linking nodes of the new self-consistent taxonomy to named organisms of the standard taxonomy. Underlying child nodes of the self-consistent taxonomy that contained k-mers (i.e., of the 170,000 genomes) not present in the standard database (i.e., RefSeq Complete) can be linked to organisms of the standard taxonomy through interior nodes of the self-consistent tree.

Figure 5:
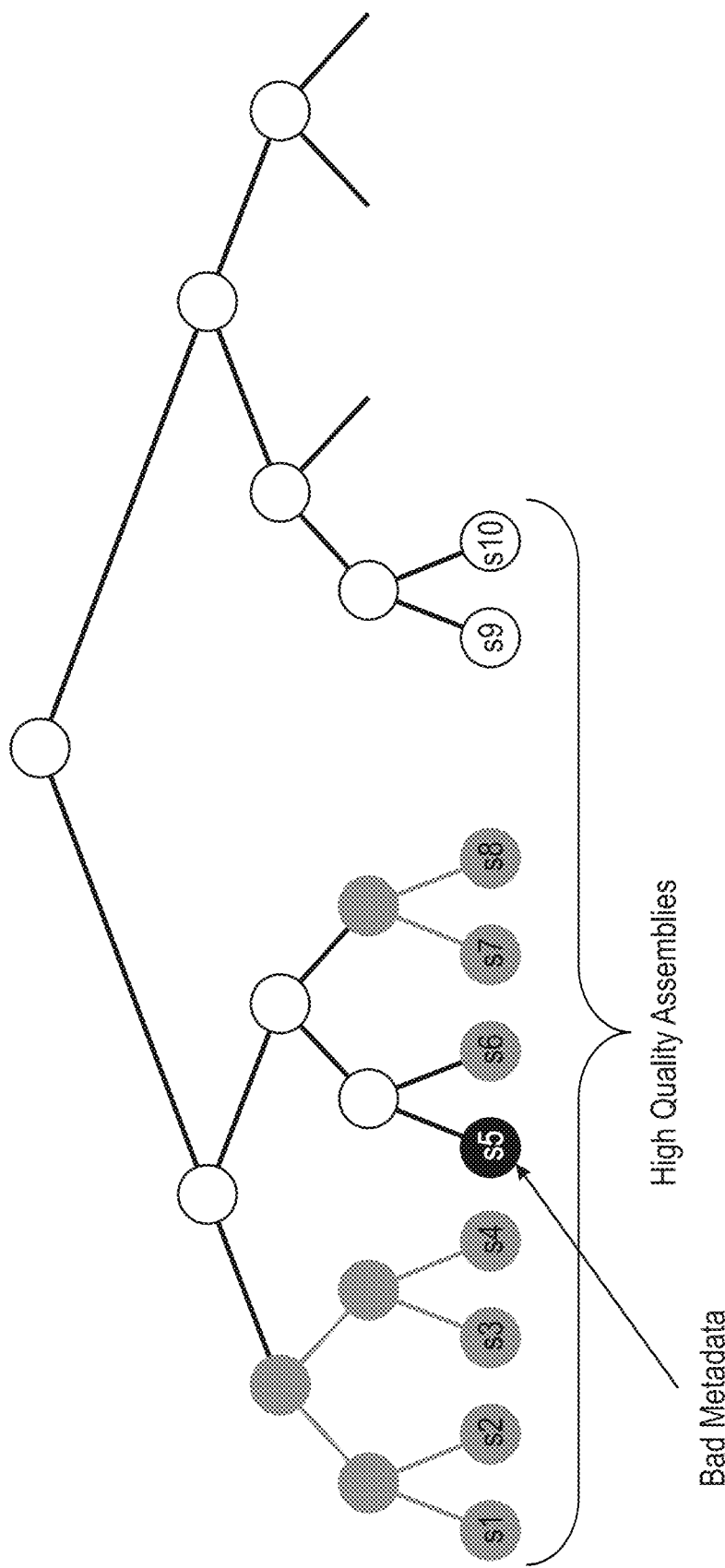
FIG. 5 is a portion of a tree diagram illustrating how a self-consistent taxonomy makes it possible to separate the problem of database construction from the problem of bad metadata. Although the SS genome contains bad metadata, the disclosed self-consistent taxonomy places the SS genome on the correct leaf node.

The self-consistent taxonomy circumvents misclassifications of the standard taxonomy as illustrated in the tree diagram of FIG. 5. Here, a series of genomes labeled s1-s4 and s6-s8 are clustered together in the self-consistent taxonomy because their genotypes are in fact similar to each other (e.g., they are all *Salmonella* genomes). The genome s5 has metadata that "label" it as *Escherichia*, but that information is not used to determine classification in the self-consistent taxonomy. Only the genetic distance is used, and since the genome s5 is in fact an example of a *Salmonella*, s5 becomes clustered with the other members of the *Salmonella* genus in the self-consistent taxonomy despite being incorrectly labeled in the metadata as *Escherichia*.

In the example of FIG. 5, the taxonomy is represented as a "binary tree", the typical output structure for a hierarchical clustering algorithm. In a binary tree structure, each parent node can have two child nodes. Each node of the self-consistent taxonomy is assigned a map relating a set of reportable standard IDs to that node's self-consistent ID. Leaf nodes in the standard binary tree (FIG. 5) have only one genome. Therefore, a given leaf node of the self-consistent taxonomy has only one standard ID mapping to one self-consistent ID. Higher level "parent nodes" (interior nodes) of the self-consistent taxonomy, identified by a single unique self-consistent ID, contain a "taxonomy map", which links each standard ID found below a given parent node with the number of child nodes in which that standard ID occurs.

In summary, a given record of the self-consistent k-mer database comprises a k-mer, a self-consistent ID assigned to the k-mer, one or more standard IDs of the standard taxonomy mapped to the self-consistent IDs of the self-consistent taxonomy, respective weights and/or respective probabilities of each of the standard IDs, and other optional data of the standard database if desired.

Condensing the Taxonomy

With this mapping, it is possible (optionally) to condense the tree in every place where the metadata are consistent with the self-consistent taxonomy and pairs of nodes within the binary tree have the same standard ID. Any node whose taxonomy map contains one and only one standard ID can be trimmed so long as its parent node contains one and only one standard ID. This effectively condenses the tree by combining all similar genomes with the same standard ID onto one node. It also preserves the child node "count" that reflects the quantitative weight of evidence below a given parent node. After this condensation step, a given node on the tree has its own unique self-consistent ID and a taxonomy map associating each standard ID with a weight equal to the number of genomes with that standard ID at or below the given node. The mapping is illustrated in Table 1 below. Each weight of Table 1 can have a whole number value greater than or equal to 1. Subscripts a, b, and c of Table 1 refer to different nodes of the self-consistent taxonomy, with correspondingly uniquely assigned self-consistent IDs. Similarly, subscripts i, j, k, x, y, and w of Table 1 refer to different nodes of the standard taxonomy, with correspondingly uniquely assigned standard IDs and their calculated weights.

TABLE 1

| | | | | | | |
|---|---|---|---|---|---|---|
| self-consistent $ID_a$ | reference $ID_i$ | $weight_i$ | reference $ID_j$ | $weight_j$ | reference $ID_k$ | $weight_k$ |
| self-consistent $ID_b$ | reference $ID_x$ | $weight_x$ | | | | |
| self-consistent $ID_c$ | reference $ID_y$ | $weight_y$ | reference $ID_w$ | $weight_w$ | | |

As a non-limiting example, a self-consistent k-mer database designed to identify organisms at the species level can have a high level parent node having 1000 linked child nodes all containing the standard ID of one single species (e.g., *Salmonella enterica*). In this instance, the 1000 linked child nodes of the self-consistent k-mer database can be removed, leaving the high level parent node linked to a standard ID for *Salmonella enterica* having a weight of 1000.

Figure 6:
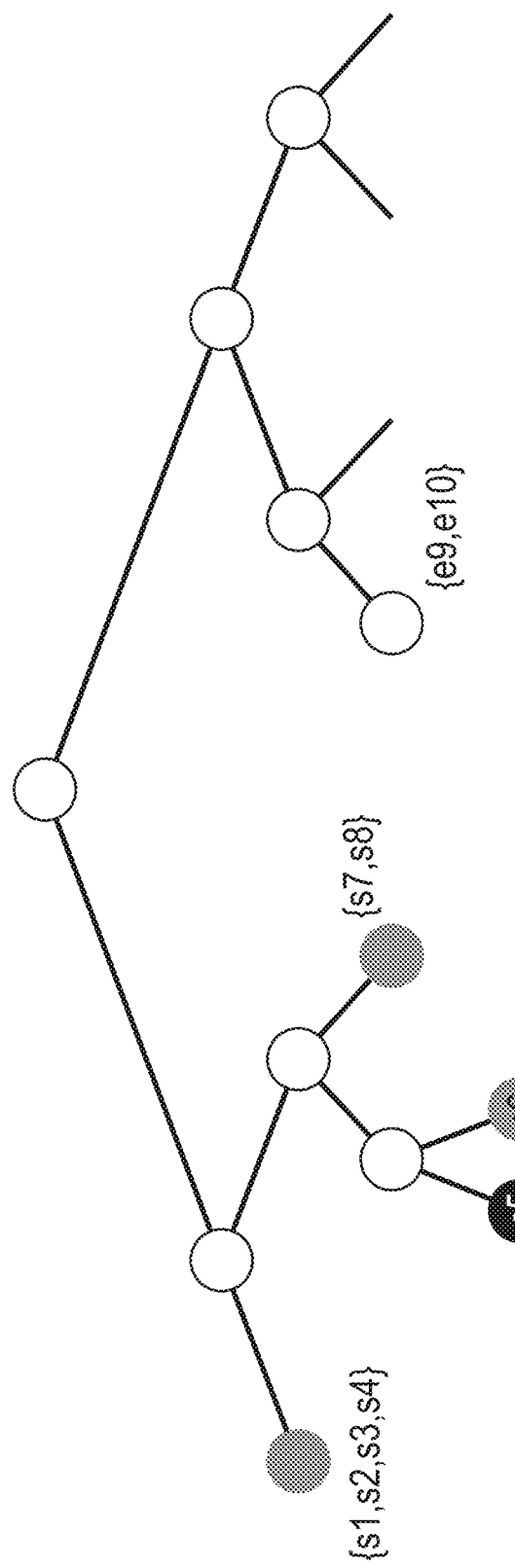
FIG. 6 is a portion of a tree diagram illustrating condensation of nodes of the taxonomic tree when the database utilizes self-consistent taxonomic IDs. The taxonomy can be condensed, taking advantage of every place a reference taxonomy is correct, by grouping all leaf nodes with common reference IDs onto one tree node.

An important feature of this approach to condensation is that it takes advantage of every place the self-consistent taxonomy is in agreement with the standard taxonomy and yet is robust against errors of the standard taxonomy. FIG. 6 again shows genome s5, which is *Salmonella* but is incorrectly labeled as *Escherichia*. Using the method described above, if this error is left uncorrected then that part of the taxonomic tree is left expanded. This means the unique k-mers do not move up to a higher taxonomic level (e.g., lowest common ancestor), thereby preserving the specificity of the database with respect to the self-consistent taxonomy. When the database is used to identify organisms within a metagenomic sample, the evidence for all possible standard IDs is reported based on the weights associated with that ID. In the case of a sample containing *Salmonella enterica*, the reads with k-mers unique to *Salmonella enterica* will be reported (post-process) in the standard taxonomy as the standard ID for *Salmonella enterica* with a weight of 1000, and *Escherichia* with a weight of 1. The probability of *Salmonella enterica* is then 1000/1001 while the probability of some *Escherichia* strain is only $1/1000$. Thus, the database report is robust against errors in the metadata. Database performance can be further improved by correcting those metadata errors.

Discontinuities of the standard taxon mapping in the self-consistent taxonomy can be favorably used to identify clerical errors and/or apparent errors of the metadata of the standard databases, reveal inaccuracies in the standard taxonomy structure, discover gene movement between organisms (i.e., horizontal gene transfer) that re-orients the organism into a new taxon category, and/or highlight areas of the taxon and database construction that needs attention for correction in order to increase accuracy of the self-consistent k-mer database. Moreover, the self-consistent k-mer database can be designed to be sensitive to specific standard taxon levels by collapsing or expanding taxon nodes based on common reference IDs. These advantages carry through the presently disclosed methods when the self-consistent k-mer database is used as the reference database.

Reporting

FIG. 7 is a sample of tabulated probabilistic report data available after k-mer analysis of sample data using the self-consistent k-mer database. The first column in the report table contains the self-consistent IDs of the database, and the second column contains the number of k-mers (or, alternatively, number of reads), assigned to each self-consistent ID. The subsequent columns are paired and enumerate all of the standard IDs linked to each self-consistent ID along with the probability assigned to each of the linked standard IDs. If there is only one linked standard ID, its probability is 1.0. If there are multiple linked standard IDs, then their probabilities add to 1.0.

Reporting can then be done by providing a probabilistic report such as, for example, the product of each standard ID probability with the k-mer or read count for each standard ID, and totaling by standard ID for all IDs, or by applying other rules (e.g., summing only the standard IDs with greatest probability at each self-consistent ID.

Taxonomic Profiling Using the Self-Consistent k-Mer Database as Reference Database This section provides more detail of the process of profiling nucleic acids of a sample using the self-consistent k-mer database as the reference database in conjunction with a computer system. The method is depicted in the flow diagram of FIGS. 8A-8G.

A sample is provided for analysis containing nucleic acids of one or more organisms therein (FIG. 8A). The nucleic acids can be of eukaryotic and/or prokaryotic origin. In an embodiment, the sample comprises nucleic acids of one or more prokaryotic microorganisms. Non-limiting examples of samples include water samples obtained from tap water, lakes, streams, field runoff, and sewage; swabbed samples from contact surfaces (e.g., building surfaces, countertops, furniture, utensils, clinical instruments, computer hardware, cell phones, door handles, doors, windows, screens, cabinets, cabinet doors, sinks, faucet); animal samples (e.g., blood, blood plasma, serum, cells, a cellular extract, a cellular aspirate, expectorant, sputum, saliva, mucous, urine, sweat, tears); and samples obtained from food, food-handling equipment, and surfaces contacted by food. The samples can be a solid or liquid containing water or no water.

RNA and/or DNA can be extracted from the working sample and subjected to high throughput sequencing (FIG. 8B).

Optionally, quality control of sequence data of the working sample is performed by removing data of poor quality, removing sequences introduced by the sequencing methodology, and/or removing any contaminating sequences (FIG. 8C).

Optionally, the sequences are assembled to contigs (FIG. 8D). K-mers of the sequences/contigs are then mapped to the genomes of the self-consistent k-mer database using k-mer substraction and/or assigned taxonomic thresholds in order to accommodate available computer memory as described further above (FIG. 8E). The contigs can be mapped to the reference genome using Burrows-Wheeler transformation based method or a similar technique.

The per-position-coverage and windows of the mapped sequences or mapped contigs are then determined (FIG. 8F). Coverage thresholds for the mapped sequences or mapped contigs are then calculated. Optionally, the mapped sequences or mapped contigs can be filtered based on coverage threshold. Optionally, the sequence coverage data can be smoothed using a generic method (e.g., LOESS) to remove coverage spikes arising from technical biases. A more specialized method that takes into account specific genome characteristics can also be used if that information is available. From the coverage data, at least one organism of the sample is identified (FIG. 8G).

Metagenomic and metatranscriptomic sequences obtained by high throughput sequencing of an environmental sample can be passed to publicly available intermediary programs such as BLAST for aligning k-mers of the sequences of the environmental sample to the k-mers of the self-consistent k-mer database, thereby identifying which organisms of the self-consistent taxonomy, if any, are most likely to be present in the sample. Optionally, the intermediary program can conduct alignment of sequence data of the sample to raw sequences, contigs, and/or whole genomes from which the k-mers of the self-consistent k-mer database originated in order to increase specificity of the organism identification. The intermediary program can perform a simple database search on a sample sequence, or alternatively, conduct pairwise sequence alignments, multiple sequence alignments, and/or pairwise genome alignments.

Other non-limiting software programs for aligning metagenomic and metatranscriptomic sequences to the sequence data of the self-consistent taxonomy include FASTA (simple search), ALLALIGN (pairwise, multiple alignments), BLASTZ (pairwise), DNASTAR (pairwise, multiple), AVID (pairwise genome), GMAP (genome alignment), and MGA (multiple genome alignment).

Queries

This section generally applies to searches other than for classification purposes. For comparison, in a Kraken classification search, the data to be classified (e.g., a read) are processed to extract from them every k-mer in the read. Each k-mer is then compared to the entire self-consistent k-mer reference database and if there is a hit, then a counter representing evidence for the taxonomic ID of the node it hits is incremented. When this is complete, the total hits from all k-mers are tallied and summarized in a report by node ID. Any k-mer in the read but not in the database is tallied as "not found."

In a search other than for classification purposes, queries can be performed on metadata information (e.g., author, date, source of the sequences, etc.), the k-mers, on the nucleic acid sequences from which the k-mers originated, on contigs of the nucleic acid sequences, on whole genomes assembled from the sequences, and/or on combinations of any of the foregoing. The k-mers, the nucleic acid sequences, the contigs, and the whole genomes can be stored in the same data table or in separate electronic files (e.g., text files such as FASTA or compressed text files such as FASTQ) that are relationally linked by index keys (e.g., the self-consistent IDs). No restriction is placed on the types of queries that can be performed, provided that the queries do not exceed the limits of the information contained in the self-consistent k-mer database and any additional tables linked thereto. Queries can be performed by manual entry of search terms, by search terms generated programmatically, or by combinations thereof.

The self-consistent k-mer database can be located at sites available to the general public and/or to specialized groups (e.g., academic, medical, forensic, environmental, governmental, and/or military). Sites include private, corporate, and/or public websites for conducting online searches. Alternatively, the self-consistent k-mer database and linked additional tables can be downloaded and stored at a local site for conducting queries using a local computer network using the disclosed methods.

Searches can be conducted at a low level using the database management software used to create the database files (e.g., by opening the self-consistent k-mer database and any additional linked tables manually and searching the opened files using command statements entered manually). Preferably, searches are performed using an intermediary software program designed to collect search terms using a graphical user interface, programmatically organize the search terms into valid query statements, open the database files, conduct searches on the database files based on the query statements, and report the results in an organized format, which can be in the form of an electronic file stored to a storage device, data displayed on a monitor, data sent to an output device (e.g., printer), and/or data passed to another program for further analysis and/or handling.

Microorganisms

Microorganisms include bacteria, fungi, viruses, protozoans, and parasites. A sample can contain microorganisms singularly or in combination.

Bacterial species can be Gram-positive or Gram-negative. Exemplary non-limiting bacterial species include *Acetobacter aurantius, Acinetobacter baumannii, Actinomyces israelii, Agrobacterium radiobacter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus Thuringiensis, Bacteroides fragilis, Bacteroides gingivalis, Bacteroides melaninogenicus* (also known as *Prevotella melaninogenica*), *Bartonella henselae, Bartonella quintana, Bordetella, Bordetella bronchiseptica, Bordetella pertussis, Borrelia afzelii, Borrelia burgdorferi, Borrelia garinii, Borrelia recurrentis, Brucella abortus, Brucella canis, Brucella melitensis, Brucella suis, Burkholderia mallei, Burkholderia pseudomallei, Burkholderia cepacia, Calymmatobacterium granulomatis, Campylobacter, Campylobacter coli, Campylobacter fetus, Campylobacter jejuni, Campylobacter pylori, Chlamydophila pneumoniae* (previously called *Chlamydia pneumoniae*), *Chlamydophila psittaci* (previously called *Chlamydia psittaci*), *Chlamydia trachomatis, Clostridium botulinum, Clostridium difficile, Clostridium perfringens* (previously called *Clostridium welchii*), *Clostridium tetani, Corynebacterium diphtheriae, Corynebacterium fusiforme, Coxiella burnetii, Ehrlichia canis, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus bulgaricus, Lactobacillus casei, Lactococcus lactis, Legionella pneumophila, Leptospira interrogans, Leptospira santarosai, Leptospira weilii, Leptospira noguchii, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycobacterium ulcerans, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica* (previously called *Bacteroides melaninogenicus*), *Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Shigella sonnei, Spirillum volutans, Streptococcus agalactiae, Staphylococcus aureus, Staphylococcus epidermidis, Staphylococcus saprophyticus, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus viridans, Treponema pallidum, Treponema denticola, Ureaplasma urealyticum, Vibrio cholerae, Vibrio comma,*

*Vibrio parahaemolyticus, Vibrio vulnificus, Yersinia enterocolitica, Yersinia pestis, Yersinia pseudotuberculosis,*

Non-limiting exemplary viruses include the family Retroviridae, such as human deficiency viruses, such as HIV-I (also referred to as HTLV-III), HIV-II, LAC, IDLV-III/LAV, HIV-III or other isolates such as HIV-LP, the family Picornaviridae, such as poliovirus, hepatitis A, enteroviruses, human Coxsackie viruses, rhinoviruses, echoviruses, the family Calciviridae, such as viruses that cause gastroenteritis, the family Togaviridae, such as equine encephalitis viruses and rubella viruses, the family Flaviviridae, such as dengue viruses, encephalitis viruses and yellow fever viruses, the family Coronaviridae, such as coronaviruses, the family Rhabdoviridae, such as vesicular stomata viruses and rabies viruses, the family Filoviridae, such as Ebola viruses, the family Paramyxoviridae, such as parainfluenza viruses, mumps viruses, measles virus and respiratory syncytial virus, the family Orthomyxoviridae, such as influenza viruses, the family Bungaviridae, such as Hataan viruses, bunga viruses, phleoboviruses and Nairo viruses, the family Arena viridae, such as hemorrhagic fever viruses, the family Reoviridae, such as reoviruses, orbiviruses and rotaviruses, the family Bimaviridae, the family Hepadnaviridae, such as hepatitis B virus, the family Parvoviridae, such as parvoviruses, the Papovaviridae, such as papilloma viruses and polyoma viruses, the family Adenoviridae, such as adenoviruses, the family Herpesviridae, such as herpes simplex virus (HSV) I and II, varicella zoster virus and pox viruses, or the family Iridoviridae, such as African swine fever virus). The virus can be an unclassified virus, such as the etiologic agents of Spongiform encephalopathies, the agent of delta hepatitis, the agents of non-A, non-B hepatitis (class 1 enterally transmitted; class 2 parenterally transmitted such as Hepatitis C); Norwalk and related viruses and astroviruses.

Other non-limiting exemplary viruses include Varicella-zoster virus, Epstein-barr virus, Human cytomegalovirus, Human herpesvirus type 8, Human papillomavirus, BK virus, JC virus, Smallpox, Parvovirus B19, poliovirus, yellow fever virus, West Nile virus, TBE virus, Rubella virus, Hepatitis E virus, Influenza virus, Lassa virus, Crimean-Congo hemorrhagic fever virus, Hantaan virus, Marburg virus, Coltivirus, Banna virus, and zika virus.

Non-limiting exemplary fungi include *Candida albicans, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii, Pneumocystis carinii,* and *Stachybotrys chartararn.*

Non-limiting exemplary protozoa include *Entamoeba histolytica, Entamoeba coli, Entamoeba dispar, Entamoeba moshkovskii, Entamoeba Bangladeshi, Entamoeba hartmanni, Dientamoeba fragilis, Endolimax nana, Iodarnoeba butschlii, Plasmodium malariae, Plasmodium falciparum, Plasmodium vivax, Plasmodium ovale, Naegleria fowleri, Acanthamoeba species, Balamuthia mandrillaris, Sappinia diploidea, Giardia larnblia, Giardia intestinalis, Giardia duodenalis, Toxoplasma gondii, Nippostrongylus brasiliensis, Cryptosporidium parvum, Cryptosporidium hominis, Cryptosporidium cams, Cryptosporidium felis, Cryptosporidium meleagridis, Cryptosporidium muris, Trichomonas vaginalis, Trypanosoma cruzi, Leishmania major, Leishmania tropica, Leishmania barziliensis, Leishmania mexicana, Leishmania guyanesis, Leishmania panamensis,* and *Trypanosoma brucei.*

Sequencing

Non-limiting methods of DNA/RNA sequencing include massively parallel signature sequencing (or MPSS), Polony sequencing, 454 pyrosequencing method, Illumina (Solexa) sequencing, SOLiD sequencing, ion semiconductor sequencing, DNA nanoball sequencing, heliscope sequencing, single molecule real time sequencing (SMRT sequencing), solid state nanopore sequencing, protein based nanopore sequencing, sequencing by electrical tunneling currents, sequencing by matrix-assisted laser desorption ionization time-of-flight mass spectrometry (MALDI-TOF MS), microfluidic Sanger sequencing, transmission electron microscopy DNA sequencing, RNA polymerase (RNAP) sequencing method, in vitro virus high throughput sequencing (IVV-HiTSeq), and sequencing by hybridization. Multiple fragmented sequence reads can be assembled together by software on the basis of their overlapping areas.

The foregoing methods of sequencing can be used singularly or in combination. The sequencing methods can be applied to genome sequencing, genome resequencing, transcriptome profiling (RNA-Seq), DNA-protein interactions (ChIP-sequencing), and epigenome characterization. Preferably, the sequencing method(s) operates in a parallel mode (characterizing many sequences concurrently).

Computer Hardware and Software

The computer system for implementing the present invention can take the form of an entirely hardware embodiment, an entirely software embodiment (including firmware, resident software, microcode, etc.), or a combination of software and hardware that may all generally be referred to herein as a "circuit," "module," or "system."

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 9:
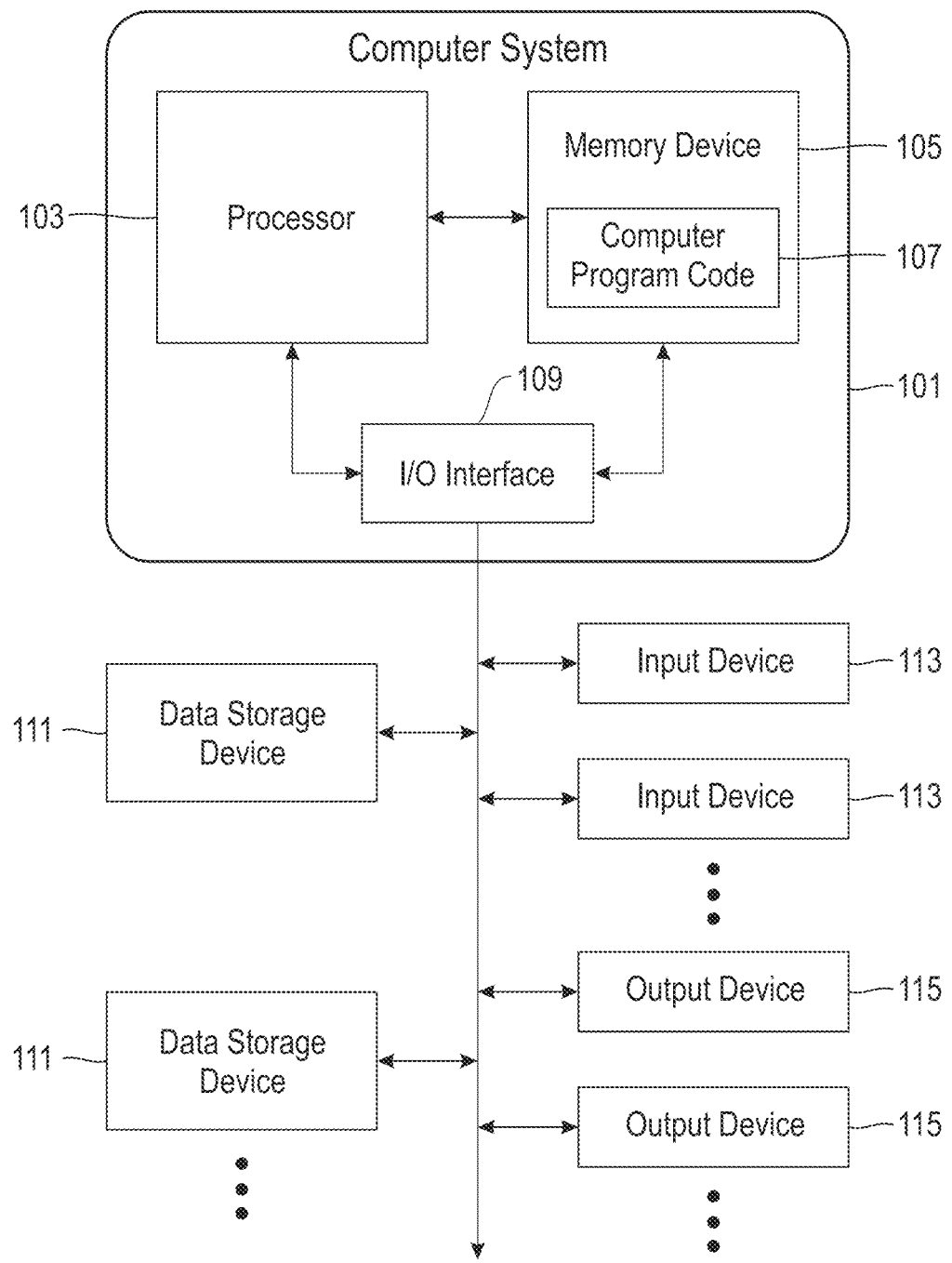
FIG. 9 is a block diagram showing a structure of a computer system and computer program code that may be used to implement a method of processing, including natural-language processing, to generate a disclosed self-consistent k-mer database from a reference k-mer database containing misclassified sequence data.

FIG. 9 shows a structure of a computer system and computer program code that may be used to implement a method of processing, including natural-language processing, to perform a classification of a sequenced sample using k-mer subtraction and/or taxonomic threshold assignments with respect to a self-consistent k-mer database used as the reference database. The computer system and program code can also be used to implement a method of processing, including natural-language processing, utilizing k-mer subtraction and/or taxonomic threshold assignments with respect to a self-consistent k-mer database when conducting taxonomic profiling of samples containing one or more organisms.

In FIG. 9, computer system 101 comprises a processor 103 coupled through one or more I/O Interfaces 109 to one or more hardware data storage devices 111 and one or more I/O devices 113 and 115. Hardware data storage devices 111 can contain the self-consistent reference k-mer database and/or the above-described groups formed therefrom by k-mer substraction and/or assignment of taxonomic thresholds.

Hardware data storage devices 111 may include, but are not limited to, magnetic tape drives, fixed or removable hard disks, optical discs, storage-equipped mobile devices, and solid-state random-access or read-only storage devices. I/O devices may comprise, but are not limited to: input devices 113, such as keyboards, scanners, handheld telecommunications devices, touch-sensitive displays, tablets, biometric readers, joysticks, trackballs, or computer mice; and output devices 115, which may comprise, but are not limited to printers, plotters, tablets, mobile telephones, displays, or sound-producing devices. Data storage devices 111, input devices 113, and output devices 115 may be located either locally or at remote sites from which they are connected to I/O Interface 109 through a network interface.

Processor 103 may also be connected to one or more memory devices 105, which may include, but are not limited to, Dynamic RAM (DRAM), Static RAM (SRAM), Programmable Read-Only Memory (PROM), Field-Programmable Gate Arrays (FPGA), Secure Digital memory cards, SIM cards, or other types of memory devices.

At least one memory device 105 contains stored computer program code 107, which is a computer program that comprises computer-executable instructions. The stored computer program code can include a program for natural-language processing that implements the disclosed methods. The data storage devices 111 may store the computer program code 107. Computer program code 107 stored in the storage devices 111 can be configured to be executed by processor 103 via the memory devices 105. Processor 103 can execute the stored computer program code 107.

Thus, the present invention discloses a process for supporting computer infrastructure, integrating, hosting, maintaining, and deploying computer-readable code into the computer system 101, wherein the code in combination with the computer system 101 is capable of performing the analysis of sequence data pertinent to classifications using k-mer subtraction and/or taxonomic thresholds with respect to the self-consistent k-mer database, and generating reports therefrom. The computer system 101 is capable of performing the analysis of sequence data of a sample pertinent to the determination of identifying species using the self-consistent k-mer database as described further above.

Any of the components of the present invention can be created, integrated, hosted, maintained, deployed, managed, serviced, supported, etc. by a service provider. Thus, the present invention discloses a process for deploying or integrating computing infrastructure, comprising integrating computer-readable code into the computer system 101, wherein the code in combination with the computer system 101 is capable of performing the analysis of sequence data pertinent to the determination of identifying the viable species of the sample.

One or more data storage units 111 (or one or more additional memory devices not shown in FIG. 9) may be used as a computer-readable hardware storage device having a computer-readable program embodied therein and/or having other data stored therein, wherein the computer-readable program comprises stored computer program code 107. Generally, a computer program product (or, alternatively, an article of manufacture) of computer system 101 may comprise said computer-readable hardware storage device.

While it is understood that program code 107 may be deployed by manually loading the program code 107 directly into client, server, and proxy computers (not shown) by loading the program code 107 into a computer-readable storage medium (e.g., computer data storage device 111), program code 107 may also be automatically or semi-automatically deployed into computer system 101 by sending program code 107 to a central server (e.g., computer system 101) or to a group of central servers. Program code 107 may then be downloaded into client computers (not shown) that will execute program code 107.

Alternatively, program code 107 may be sent directly to the client computer via e-mail. Program code 107 may then either be detached to a directory on the client computer or loaded into a directory on the client computer by an e-mail option that selects a program that detaches program code 107 into the directory.

Another alternative is to send program code 107 directly to a directory on the client computer hard drive. If proxy servers are configured, the process selects the proxy server code, determines on which computers to place the proxy servers' code, transmits the proxy server code, and then installs the proxy server code on the proxy computer. Program code 107 is then transmitted to the proxy server and stored on the proxy server.

In one embodiment, program code 107 is integrated into a client, server and network environment by providing for program code 107 to coexist with software applications (not shown), operating systems (not shown) and network operating systems software (not shown) and then installing program code 107 on the clients and servers in the environment where program code 107 will function.

The first step of the aforementioned integration of code included in program code 107 is to identify any software on the clients and servers, including the network operating system (not shown), where program code 107 will be deployed that are required by program code 107 or that work in conjunction with program code 107. This identified software includes the network operating system, where the network operating system comprises software that enhances a basic operating system by adding networking features. Next, the software applications and version numbers are identified and compared to a list of software applications and correct version numbers that have been tested to work with program code 107. A software application that is missing or that does not match a correct version number is upgraded to the correct version.

A program instruction that passes parameters from program code 107 to a software application is checked to ensure that the instruction's parameter list matches a parameter list required by the program code 107. Conversely, a parameter passed by the software application to program code 107 is checked to ensure that the parameter matches a parameter required by program code 107. The client and server operating systems, including the network operating systems, are identified and compared to a list of operating systems, version numbers, and network software programs that have been tested to work with program code 107. An operating system, version number, or network software program that does not match an entry of the list of tested operating systems and version numbers is upgraded to the listed level on the client computers and upgraded to the listed level on the server computers.

After ensuring that the software, where program code 107 is to be deployed, is at a correct version level that has been tested to work with program code 107, the integration is completed by installing program code 107 on the clients and servers.

Embodiments of the present invention may be implemented as a method performed by a processor of a computer system, as a computer program product, as a computer system, or as a processor-performed process or service for supporting computer infrastructure. The disclosed self-consistent database and/or the above-described groups of k-mers formed therefrom can be located on a cloud platform of a computer network.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A method for reducing computer memory requirements and increasing query speed to improve computational performance of a physical computer system configured to conduct taxonomic queries, comprising:
    providing a database comprising k-mers of one or more organisms classified to a taxonomy, wherein the database is greater than available computer memory of a computer system;
    in response to the database being greater than the available computer memory, dividing, by the computer system, the database into two or more independent groups of k-mers for at least organism A and organism B, wherein each of the groups comprises a unique set of nodes of the taxonomy, wherein all k-mers of a given node of nodes reside in only one of the groups and each of the groups is an independent data file;
    assigning a taxonomic threshold level of the taxonomy, wherein the taxonomic threshold level is automatically assigned by the computer system;
    providing the taxonomy as a self-consistent taxonomy that is independent of metadata associated with the k-mers from a standard taxonomy, wherein a map is generated that comprises associations of self-consistent identifications for each of the nodes in the self-consistent taxonomy to standard identifications in the standard taxonomy in response to the database being greater than the available computer memory, the self-consistent taxonomy being free of the metadata;
    removing, by the computer system, k-mers common to two or more of the groups, thereby forming two or more modified groups comprising the organism A and the organism B, each of the modified groups containing a unique set of k-mers for the organism A and the organism B, each of the modified groups being an independent data file;
    using, by the computer system, the k-mers of the modified groups as reference k-mers for comparison to computer queries and/or taxonomic classifications of k-mers of a sample in order to reduce query time and reduce computer storage on the available computer memory of the computer system, the sample comprising taxonomically unclassified sequenced nucleic acids of one or more organisms, wherein the computer queries and/or taxonomic classifications identifies at least one of the organisms of the sample;
    generating a matrix M, wherein the matrix M includes genetic distances between genomes; and
    performing a hash to determine the genetic distances, wherein the database is associated with pointers which point to rows in the database and wherein the k-mers are associated with the genomes.

2. The method of claim 1, wherein the taxonomy is based on calculated genetic distances.

3. The method of claim 2, wherein the genetic distances are genome-genome distances calculated using the MinHash algorithm.

4. The method of claim 1, wherein the modified groups are stored on different computer nodes when used for said computer queries and/or for taxonomic classifications.

5. The method of claim 1, wherein the removed k-mers are stored on a computer node separate from the modified groups.

6. The method of claim 1, wherein the removed k-mers are used to confirm identification of an organism found in the queries and/or the classifications.

7. The method of claim 1, wherein the one or more organisms are microorganisms selected from the group consisting of bacteria, fungi, viruses, protozoans, parasites, and combinations thereof.

8. The method of claim 1, wherein the sample is selected from the group consisting of environmental samples, medical samples, and food samples.

9. A method for reducing computer memory requirements and increasing query speed to improve computational performance of a physical computer system configured to conduct taxonomic queries, comprising:
    providing a database comprising k-mers of one or more organisms classified to a taxonomy, wherein the database is greater than available computer memory of a computer system;
    assigning a taxonomic threshold level of the taxonomy, wherein the taxonomic threshold level is automatically assigned by the computer system; and
    in response to the database being greater than the available computer memory, removing, by the computer system, k-mers of the database that are classified to taxonomic levels above the threshold level, thereby forming a modified database having a size in bytes less than the database and suitable for the available computer memory of the computer system;
    using, by the computer system, the k-mers of the modified database as reference k-mers for comparison to computer queries and/or taxonomic classifications of k-mers of a sample in order to reduce query time and reduce computer storage on the available computer memory of the computer system, the sample comprising taxonomically unclassified sequenced nucleic acids of one or more organisms, wherein the computer queries and/or taxonomic classifications identifies at least one of the organisms of the sample;
    providing the taxonomy as a self-consistent taxonomy that is independent of metadata associated with the k-mers from a standard taxonomy, wherein a map is generated that comprises associations of self-consistent identifications for each node in the self-consistent taxonomy to standard identifications in the standard taxonomy in response to the database being greater than the available computer memory, the self-consistent taxonomy being free of the metadata;
    generating a matrix M, wherein the matrix M includes genetic distances between genomes; and
    performing a hash to determine the genetic distances, wherein the database is associated with pointers which point to rows in the database and wherein the k-mers are associated with the genomes.

10. The method of claim 9, wherein the taxonomic threshold level is selected from the group consisting of family, genus, species, sub-species, and strain.

11. The method of claim 9, wherein the taxonomic threshold level is selected by a machine using artificial intelligence.

12. A method for reducing computer memory requirements and increasing query speed to improve computational performance of a physical computer system configured to conduct taxonomic queries, comprising:

provinding a database comprising k-mers of one or more organisms classified to a taxonomy, wherein the database is greater than available computer memory of a computer system;

assigning a taxonomic threshold level of the taxonomy, wherein the taxonomic threshold level is automatically assigned by the computer system; and in response to the database being greater than the available computer memory, removing, by the computer system, k-mers of the database that are classified to taxonomic levels above the threshold level, thereby forming a modified database;

in response to the database being greater than the available computer memory, dividing, by the computer system, the modified database into two or more independent groups of k-mers for at least organism A and organism B, wherein each of the two or more groups comprises a unique set of nodes of the taxonomy and all k-mers of a given node of nodes reside in one of the groups, and wherein each of the groups is an independent data file;

providing the taxonomy as a self-consistent taxonomy that is independent of metadata associated with the k-mers from a standard taxonomy, wherein a map is generated that comprises associations of self-consistent identifications for each of the nodes in the self-consistent taxonomy to standard identifications in the standard taxonomy in response to the database being greater than the available computer memory, the self-consistent taxonomy being free of the metadata;

in response to the database being greater than the available computer memory, removing, by the computer system, k-mers common to the two or more groups, thereby forming two or more modified groups of k-mers comprising the organism A and the organism B, wherein each of the modified groups is an independent data file;

using, by the computer system, the k-mers of the modified groups as reference k-mers for comparison to computer queries and/or taxonomic classifications of k-mers of a sample in order to reduce query time and reduce computer storage on the available computer memory of the computer system, the sample comprising taxonomically unclassified sequenced nucleic acids of one or more organisms, wherein the computer queries and/or taxonomic classifications identifies at least one of the organisms of the sample;

generating a matrix M, wherein the matrix M includes genetic distances between genomes; and performing a hash to determine the genetic distances, wherein the database is associated with pointers which point to rows in the database and wherein the k-mers are associated with the genomes.

13. The method of claim 12, wherein the modified groups are used in parallel when performing a computer query and/or taxonomic classification.

14. A computer program product, comprising a computer readable hardware storage device having a computer-readable program code stored therein, said program code configured to be executed by a processor of a computer system to implement a method for reducing computer memory requirements and increasing query speed to improve computational performance of the computer system configured to conduct taxonomic queries, comprising:

providing a database comprising k-mers of one or more organisms classified to a taxonomy, wherein the database is greater than available computer memory of the computer system;

assigning a taxonomic threshold level of the taxonomy, wherein the taxonomic threshold level is automatically assigned by the computer system;

in response to the database being greater than the available computer memory, dividing, by the processor, the database into two or more independent groups of k-mers for at least organism A and organism B, wherein each of the groups comprises a unique set of nodes of the taxonomy, wherein all k-mers of a given node nodes reside in one of the groups and each of the groups is an independent data file;

providing the taxonomy as a self-consistent taxonomy that is independent of metadata associated with the k-mers from a standard taxonomy, wherein a map is generated that comprises associations of self-consistent identifications for each of the nodes in the self-consistent taxonomy to standard identifications in the standard taxonomy in response to the database being greater than the available computer memory, the self-consistent taxonomy being free of the metadata;

in response to the database being greater than the available computer memory, removing, by the processor, k-mers common to two or more of the groups, thereby forming two or more modified groups comprising the organism A and the organism B, each of the modified groups containing a unique set of k-mers for the organism A and the organism B, each of the modified groups being an independent data file;

using, by the processor, the k-mers of the modified groups as reference k-mers for comparison to computer queries and/or taxonomic classifications of k-mers of a sample in order to reduce query time and reduce computer storage on the available computer memory of the computer system, the sample comprising taxonomically unclassified sequenced nucleic acids of one or more organisms, wherein the computer queries and/or taxonomic classifications identifies at least one of the organisms of the sample;

generating a matrix M, wherein the matrix M includes genetic distances between genomes; and performing a hash to determine the genetic distances, wherein the database is associated with pointers which point to rows in the database and wherein the k-mers are associated with the genomes.

15. A computer program product, comprising a computer readable hardware storage device having a computer-readable program code stored therein, said program code configured to be executed by a processor of a computer system to implement a method for reducing computer memory requirements and increasing query speed to improve computational performance of the computer system configured to conduct taxonomic queries, comprising:

providing a database comprising k-mers of one or more organisms classified to a taxonomy, wherein the database is greater than available computer memory of the computer system;

assigning a taxonomic threshold level of the taxonomy, wherein the taxonomic threshold level is automatically assigned by the computer system; and in response to the database being greater than the available computer memory, removing, by the processor, k-mers of the database that are classified to taxonomic levels above the threshold level, thereby forming a modified database having a size in bytes less than the database;

using, by the processor, the k-mers of the modified database as reference k-mers for computer queries and/or taxonomic classifications of k-mers of a sample in order to reduce query time and reduce computer storage on the available computer memory of the computer system, the sample comprising taxonomically unclassified sequenced nucleic acids of one or more organisms, wherein the computer queries and/or taxonomic classifications identifies at least one of the organisms of the sample;

providing the taxonomy as a self-consistent taxonomy that is independent of metadata associated with the k-mers from a standard taxonomy, wherein a map is generated that comprises associations of self-consistent identifications for each node in the self-consistent taxonomy to standard identifications in the standard taxonomy in response to the database being greater than the available computer memory, the self-consistent taxonomy being free of the metadata;

generating a matrix M, wherein the matrix M includes genetic distances between genomes; and performing a hash to determine the genetic distances, wherein the database is associated with pointers which point to rows in the database and wherein the k-mers are associated with the genomes.

16. A system comprising one or more computer processor circuits configured and arranged to implement a method for reducing computer memory requirements and increasing query speed to improve computational performance of a physical computer system configured to conduct taxonomic queries, the system comprising:

provide a database comprising k-mers of one or more organisms classified to a taxonomy, wherein the database is greater than available computer memory of a computer system;

in response to the database being greater than the available computer memory, divide, by the one or more computer processor circuits, the database into two or more independent groups of k-mers for at least organism A and organism B, wherein each of the groups comprises a unique set of nodes of the taxonomy, wherein all k-mers of a given node of nodes reside in one of the groups, and wherein each of the groups is an independent data file;

assigning a taxonomic threshold level of the taxonomy, wherein the taxonomic threshold level is automatically assigned by the computer system;

providing the taxonomy as a self-consistent taxonomy that is independent of metadata associated with the k-mers from a standard taxonomy, wherein a map is generated that comprises associations of self-consistent identifications for each of the nodes in the self-consistent taxonomy to standard identifications in the standard taxonomy in response to the database being greater than the available computer memory, the self-consistent taxonomy being free of the metadata;

in response to the database being greater than the available computer memory, remove, by the one or more computer processor circuits, k-mers common to two or more of the groups, thereby forming two or more modified groups comprising the organism A and the organism B, each of the modified groups containing a unique set of k-mers for the organism A and the organism B, wherein each of the modified groups is an independent data file;

using, by the one or more computer processor circuits, the k-mers of the modified groups as reference k-mers for comparison to computer queries and/or taxonomic classifications of k-mers of a sample in order to reduce query time and reduce computer storage on the available computer memory of the computer system, the sample comprising taxonomically unclassified sequenced nucleic acids of one or more organisms, wherein the computer queries and/or taxonomic classifications identifies at least one of the organisms of the sample;

generating a matrix M, wherein the matrix M includes genetic distances between genomes; and performing a hash to determine the genetic distances, wherein the database is associated with pointers which point to rows in the database and wherein the k-mers are associated with the genomes.

17. The system of claim 16, wherein the modified groups are located on a cloud platform of a computer network.

18. The system of claim 16, wherein the system is configured and arranged to assign a taxonomic threshold level of the taxonomy and remove k-mers of the database that are classified to taxonomic levels above the threshold level.

19. The system of claim 16, wherein k-mers associated with mobile elements of genomes are removed from the database before the k-mers are classified to the taxonomy.

* * * * *